(12) United States Patent
Fukuda et al.

(10) Patent No.: US 10,695,396 B2
(45) Date of Patent: Jun. 30, 2020

(54) MALIGNANT TUMOR TARGET PEPTIDE

(71) Applicant: NATIONAL INSTITUTE OF ADVANCED INDUSTRIAL SCIENCE AND TECHNOLOGY, Tokyo (JP)

(72) Inventors: Michiko Fukuda, Tsukuba (JP); Motohiro Nonaka, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/326,120

(22) PCT Filed: Aug. 16, 2017

(86) PCT No.: PCT/JP2017/030003
§ 371 (c)(1),
(2) Date: Feb. 15, 2019

(87) PCT Pub. No.: WO2018/034356
PCT Pub. Date: Feb. 22, 2018

(65) Prior Publication Data
US 2019/0175684 A1    Jun. 13, 2019

(30) Foreign Application Priority Data
Aug. 16, 2016    (JP) .................... 2016-159743

(51) Int. Cl.
| | |
|---|---|
| A61K 38/03 | (2006.01) |
| A61K 38/06 | (2006.01) |
| A61K 49/04 | (2006.01) |
| A61K 49/14 | (2006.01) |
| A61P 35/00 | (2006.01) |
| A61K 49/06 | (2006.01) |
| C07K 14/00 | (2006.01) |
| A61K 45/00 | (2006.01) |
| C07K 19/00 | (2006.01) |
| C07K 7/06 | (2006.01) |
| C07K 5/08 | (2006.01) |
| C07K 5/10 | (2006.01) |
| A61K 47/64 | (2017.01) |
| A61K 49/08 | (2006.01) |
| C12N 15/09 | (2006.01) |

(52) U.S. Cl.
CPC .............. *A61K 38/03* (2013.01); *A61K 38/06* (2013.01); *A61K 45/00* (2013.01); *A61K 47/64* (2017.08); *A61K 49/04* (2013.01); *A61K 49/06* (2013.01); *A61K 49/085* (2013.01); *A61K 49/14* (2013.01); *A61P 35/00* (2018.01); *C07K 5/08* (2013.01); *C07K 5/10* (2013.01); *C07K 7/06* (2013.01); *C07K 14/00* (2013.01); *C07K 19/00* (2013.01); *C12N 15/09* (2013.01)

(58) Field of Classification Search
CPC ........................................................ C07K 7/06
See application file for complete search history.

(56) References Cited

FOREIGN PATENT DOCUMENTS

WO    WO 2010/022444 A1    3/2010
WO    WO 2015/016768 A1    2/2015

OTHER PUBLICATIONS

Falini et al (The Lancet, 2004, vol. 363, pp. 1869-1871) (Year: 2004).*
Translation of WO2018034356, downloaded from ESPACE on Feb. 5, 2020 (Year: 2020).*
Chen et al., "Retro-Inverso Carbohydrate Mimetic Peptides with Annexin1-Binding Selectivity, Are Stable in Vivo, and Target Tumor Vasculature," *PLoS One*, 8(12): e80390 (2013).
Fukuda et al., "A Peptide Mimic of E-Selectin Ligand Inhibits Sialyl Lewis X-dependent Lung Colonization of Tumor Cells," *Cancer Res.*, 60(2): 450-456 (2000).
Guo et al., "Antiproliferative and antitumor activities of D-reverse peptides derived from the second type-1 repeat of thrombospondin-1," *J. Pept. Res.*, 50(3): 210-221 (1997).
Hatakeyama et al., "Targeted drug delivery to tumor vasculature by a carbohydrate mimetic peptide," *Proc. Natl. Acad. Sci. U.S.A.*, 108(49): 19587-19592 (2011).
Hatakeyama et al., "Development of prostate cancer targeting chemotherapy utilizing annexin A1 in tumor vasculature," *Japanese Journal of Urological Surgery*, 26(8): 1203-1206 (2013).
Oh et al., "Subtractive proteomic mapping of the endothelial surface in lung and solid tumours for tissue-specific therapy," *Nature*, 429(6992): 629-635 (2004).

(Continued)

*Primary Examiner* — Karen A. Canella
(74) *Attorney, Agent, or Firm* — Leydig, Voit & Mayer, Ltd.

(57) ABSTRACT

The present invention provides a peptide comprising the amino acid sequence of any of the formulas (I)-(III) below:

(I) an amino acid sequence of (X1)[D]P[D](X2)[D] wherein X1 is W or F, X2 is S or T, and each amino acid symbol immediately followed by symbol [D] is a D form of the amino acid, (II) an amino acid sequence of P[D]T[D](X)$_n$ F[D] wherein (X)$_n$ is any amino acid in the number of n selected independently of each other, n is an integer of 0-4, and the symbol [D] is as defined above, (III) an amino acid sequence that is a Retro-inverso of the amino acid sequence of any of the aforementioned (I) and the aforementioned (II);

and a conjugate containing the peptide and a functional part.

15 Claims, 9 Drawing Sheets
(8 of 9 Drawing Sheet(s) Filed in Color)
Specification includes a Sequence Listing.

(56) References Cited

OTHER PUBLICATIONS

Xie et al., "Retro-inverso bradykinin opens the door of blood-brain tumor barrier for nanocarriers in glioma treatment," *Cancer Lett.*, 369(1): 144-151 (2015).
Japanese Patent Office, International Search Report in International Patent Application No. PCT/JP2017/030003 (dated Nov. 28, 2017).
Japanese Patent Office, Written opinion of the International Searching Authority in International Patent Application No. PCT/JP2017/030003 (dated Nov. 28, 2017).
Caron et al., "Annexin A1 is regulated by domains cross-talk through post-translational phosphorylation and SUMOYlation," *Cell. Signal.*, 25(10): 1962-1969 (2013).
Horlacher et al., "Characterization of Annexin Al Glycan Binding Reveals Binding to Highly Sulfated Glycans with Preference for Highly Sulfated Heparan Sulfate and Heparin," *Biochemistry*, 50(13): 2650-2659 (2011).

\* cited by examiner bars; 1 mm bars; 40 μm

SEQUENCE LISTING

<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 1

Met Thr Pro Trp Thr Ile Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 2

Leu Val Thr Pro Phe Arg Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 3

Ala Ser Pro Trp Ser Leu Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 4

Phe Leu Leu Ser Thr Pro Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 5

Arg Phe Thr Leu Thr Pro Met
1               5

<210> SEQ ID NO 6
<211> LENGTH: 1556
<212> TYPE: DNA
<213> ORGANISM: Homo sapiens

<400> SEQUENCE: 6
acttgtttca ctttgttttt ggacatagct gagccatgta cttcaaacag aaggcagcca        60
attactaact tctggttgct aggtgtggct tcctttaaaa tcctataaaa tcagaagccc       120

-continued

```
aagtctccac tgccagtgtg aaatcttcag agaagaattt ctctttagtt ctttgcaaga      180
aggtagagat aaagacactt tttcaaaaat ggcaatggta tcagaattcc tcaagcaggc      240
ctggtttatt gaaatgaag agcaggaata tgttcaaact gtgaagtcat ccaaaggtgg       300
tcccggatca gcggtgagcc cctatcctac cttcaatcca tcctcggatg tcgctgcctt      360
gcataaggcc ataatggtta aggtgtgga tgaagcaacc atcattgaca ttctaactaa       420
gcgaaacaat gcacagcgtc aacagatcaa agcagcatat ctccaggaaa caggaaagcc      480
cctggatgaa acactgaaga aagcccttac aggtcacctt gaggaggttg ttttagctct      540
gctaaaaact ccagcgcaat ttgatgctga tgaacttcgt gctgccatga agggccttgg      600
aactgatgaa gatactctaa ttgagatttt ggcatcaaga actaacaaag aaatcagaga      660
cattaacagg gtctacagag aggaactgaa gagagatctg ccaaagaca taacctcaga       720
cacatctgga gattttcgga acgctttgct ttctcttgct aagggtgacc gatctgagga      780
ctttggtgtg aatgaagact ggctgattc agatgccagg gccttgtatg aagcaggaga      840
aaggagaaag gggacagacg taaacgtgtt caataccatc cttaccacca gaagctatcc      900
acaacttcgc agagtgtttc agaaatacac caagtacagt aagcatgaca tgaacaaagt      960
tctggacctg gagttgaaag gtgacattga aaatgcctc acagctatcg tgaagtgcgc      1020
cacaagcaaa ccagctttct ttgcagagaa gcttcatcaa gccatgaaag gtgttggaac      1080
tcgccataag gcattgatca ggattatggt ttcccgttct gaaattgaca tgaatgatat      1140
caaagcattc tatcagaaga tgtatggtat ctccctttgc aagccatcc tggatgaaac      1200
caaaggagat tatgagaaaa tcctggtggc tctttgtgga ggaaactaaa cattcccttg      1260
atggtctcaa gctatgatca gaagacttta attatatatt ttcatcctat aagcttaaat      1320
aggaaagttt cttcaacagg attacagtgt agctacctac atgctgaaaa atatagcctt      1380
taaatcattt ttatattata actctgtata atagagataa gtccattttt taaaaatgtt      1440
ttccccaaac cataaaaccc tatacaagtt gttctagtaa caatacatga gaaagatgtc      1500
tatgtagctg aaaataaaat gacgtcacaa gacaaaaaaa aaaaaaaaa aaaaaa          1556
```

<210> SEQ ID NO 7
<211> LENGTH: 346
<212> TYPE: PRT
<213> ORGANISM: Homo sapiens

<400> SEQUENCE: 7

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125
```

Gly Leu Gly Thr Asp Glu Asp Thr Leu Ile Glu Ile Leu Ala Ser Arg
        130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 8
<211> LENGTH: 1395
<212> TYPE: DNA
<213> ORGANISM: Mus musculus

<400> SEQUENCE: 8
gtctgaaacc atctgagcag agtctctctt cagtccccgg gaagacaagc aaatacaaag    60
atacttctct aaaatggca atggtatcag aattcctcaa gcaggcccgt tttcttgaaa    120
atcaagaaca ggaatatgtt caagctgtaa atcatacaa aggtggtcct gggtcagcag    180
tgagccccta cccttccttc aatgtatcct cggatgttgc tgccttgcac aaagctatca    240
tggttaaagg tgtggatgaa gcaaccatca ttgacattct taccaagagg accaatgctc    300
agcgccagca gatcaaggcc gcgtacttac aggagaatgg aaagcccttg gatgaagtct    360
tgagaaaagc ccttacaggc cacctggagg aggttgtttt ggctatgcta aaaactccag    420
ctcagtttga tgcagatgaa ctccgtggtg ccatgaaggg acttgaaaca gatgaagaca    480
ctctcattga gattttgaca acaagatcta cgaacaaat cagagagatt aatagagtct    540
acagagaaga gctgaaaaga gatctggcca agacatcac ttcagataca tctggagact    600 tcggaaagc cttgcttgct cttgccaagg gtgaccgttg tcaggacttg agtgtgaatc    660
aagatttggc tgatacagat gccagggctt tgtatgaagc tggagaaagg agaaagggga    720
cagacgtgaa cgtcttcacc acaattctga ccagcaggag ctttcctcat cttcgcagag    780
tgtttcagaa ttacgaaag tacagtcaac atgacatgaa caaagctctg gatctggaac    840

```
tgaagggtga cattgagaag tgcctcacaa ccatcgtgaa gtgtgccacc agcactccag    900
ctttctttgc cgagaagctg tacgaagcca tgaagggtgc cggaactcgc cataaggcat    960
tgatcaggat tatggtctcc cgttcggaaa ttgacatgaa tgaaatcaaa gtattttacc   1020
agaagaagta tggaatctct ctttgccaag ccatcctgga tgaaaccaaa ggagactatg   1080
aaaaaatcct ggtggctctg tgtggtggaa actagacatc ccaactattc tgcaaggttc   1140
tgaggagaat gtctcttagc tgttttcctt cgatggcatg ggcttaagta ggaaagttgc   1200
tttggcagat aagtctaatt acctgctttg aataatatag cctataaata gattttacat   1260
cattactctg tacaatagag aaatacttgt tttgttaatt atgtttatcc caaattataa   1320
agccccataa gcaagtcact ttggtaccat tcctgagaaa gaagtttaca tataataaaa   1380
taaaacaatt ttata                                                    1395
```

<210> SEQ ID NO 9
<211> LENGTH: 346
<212> TYPE: PRT
<213> ORGANISM: Mus musculus

<400> SEQUENCE: 9

```
Met Ala Met Val Ser Glu Phe Leu Lys Gln Ala Arg Phe Leu Glu Asn
1               5                   10                  15

Gln Glu Gln Glu Tyr Val Gln Ala Val Lys Ser Tyr Lys Gly Gly Pro
            20                  25                  30

Gly Ser Ala Val Ser Pro Tyr Pro Ser Phe Asn Val Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Thr Asn Ala Gln Arg Gln Gln Ile
65                  70                  75                  80

Lys Ala Ala Tyr Leu Gln Glu Asn Gly Lys Pro Leu Asp Glu Val Leu
                85                  90                  95

Arg Lys Ala Leu Thr Gly His Leu Glu Glu Val Val Leu Ala Met Leu
            100                 105                 110

Lys Thr Pro Ala Gln Phe Asp Ala Asp Glu Leu Arg Gly Ala Met Lys
        115                 120                 125

Gly Leu Gly Thr Asp Glu Asp Thr Leu Ile Glu Ile Leu Thr Thr Arg
    130                 135                 140

Ser Asn Glu Gln Ile Arg Glu Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Lys Ala Leu Leu Ala Leu Ala Lys Gly Asp Arg Cys Gln Asp Leu
            180                 185                 190

Ser Val Asn Gln Asp Leu Ala Asp Thr Asp Ala Arg Ala Leu Tyr Glu
        195                 200                 205

Ala Gly Glu Arg Arg Lys Gly Thr Asp Val Asn Val Phe Thr Thr Ile
    210                 215                 220

Leu Thr Ser Arg Ser Phe Pro His Leu Arg Arg Val Phe Gln Asn Tyr
225                 230                 235                 240

Gly Lys Tyr Ser Gln His Asp Met Asn Lys Ala Leu Asp Leu Glu Leu
                245                 250                 255

Lys Gly Asp Ile Glu Lys Cys Leu Thr Thr Ile Val Lys Cys Ala Thr
            260                 265                 270
```

```
Ser Thr Pro Ala Phe Phe Ala Glu Lys Leu Tyr Glu Ala Met Lys Gly
            275                 280                 285

Ala Gly Thr Arg His Lys Ala Leu Ile Arg Ile Met Val Ser Arg Ser
            290                 295                 300

Glu Ile Asp Met Asn Glu Ile Lys Val Phe Tyr Gln Lys Lys Tyr Gly
305                 310                 315                 320

Ile Ser Leu Cys Gln Ala Ile Leu Asp Glu Thr Lys Gly Asp Tyr Glu
            325                 330                 335

Lys Ile Leu Val Ala Leu Cys Gly Gly Asn
            340                 345
```

```
<210> SEQ ID NO 10
<211> LENGTH: 7
<212> TYPE: PRT
<213> ORGANISM: Artificial Sequence
<220> FEATURE:
<223> OTHER INFORMATION: Synthetic tumor-targeting peptide

<400> SEQUENCE: 10

Ile Phe Leu Leu Trp Gln Arg
1               5

<210> SEQ ID NO 11
<211> LENGTH: 15
<212> TYPE: PRT
<213> ORGANISM: Homo sapiens

<400> SEQUENCE: 11

Met Ala Met Val Ser Glu Phe Leu Lys Gln Ala Trp Phe Ile Glu
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic TIT7 sequence

<400> SEQUENCE: 12

Thr Ile Thr Trp Pro Thr Met
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic random peptide

<400> SEQUENCE: 13

Leu Arg Phe Pro Thr Val Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic random peptide

<400> SEQUENCE: 14

Ser Pro Thr Ser Leu Leu Phe
1               5
```

-continued

```
<210> SEQ ID NO 15
<211> LENGTH: 7
<212> TYPE: PRT
<213> ORGANISM: Artificial Sequence
<220> FEATURE:
<223> OTHER INFORMATION: Synthetic random peptide

<400> SEQUENCE: 15

Met Pro Thr Leu Thr Phe Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic random peptide

<400> SEQUENCE: 16

Leu Lys Gly Met Leu Arg Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic random peptide

<400> SEQUENCE: 17

Leu Leu Ser Trp Pro Ser Ala
1               5
```

MALIGNANT TUMOR TARGET PEPTIDE

CROSS-REFERENCE TO RELATED APPLICATIONS

This patent application is the U.S. national phase of International Patent Application No. PCT/JP2017/030003, filed on Aug. 16, 2017, which claims the benefit of Japanese Patent Application No. 2016-159743, filed Aug. 16, 2016, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,818 bytes ASCII (Text) file named "741854SequenceListing.txt," created Feb. 12, 2019.

TECHNICAL FIELD

The present invention generally relates to the field of cancer biology, and more particularly to peptides that bind to annexin A1 and use thereof.

BACKGROUND ART

Among brain tumors, many tumors originating from meninges, brain or spinal nerve, such as meningiomas and schwannomas, are benign brain tumors and can be completely cured if they can be removed by surgery. In contrast, neuroepithelial tumors including glioma are basically malignant brain tumors. Especially, grade 4 glioblastoma shows extremely poor prognosis (5-year survival rate is about 10%) even if radiation therapy and chemotherapy are performed after removal by craniotomy. A major reason for the lack of effective chemotherapy for brain tumor is the presence of a blood-brain barrier. On the other hand, temozolomide, which is a new drug effective for glioblastoma, was approved in Japan in 2006. This drug has a very small molecular weight (194 Da) and was clarified to be able to cross the blood-brain barrier by diffusion. However, the drug has only been able to extend life expectancy from 12 months to 16 months. To dramatically improve the treatment results for malignant brain tumor in the future, therefore, it is essential to develop a therapeutic drug that accumulates in the brain tumor at an overwhelmingly high concentration and can actively cross the wall of vascular endothelium, rather than a passive method relying on the diffusion of small molecules as for the blood-brain barrier.

Recently, the economic burden on patients is becoming increasingly heavy due to the rising research and development expenses and the widespread use of antibody pharmaceuticals. In the future, this trend is considered to be further accelerated by the sophistication of medical care such as diagnosis system by genetic information and the like. In addition, the impact of these soaring drug prices on national health care costs is also immeasurable. Furthermore, expensive antibody pharmaceuticals become inaccessible to underdeveloped countries, leading to further medical inequality on a global scale. If measures are to be taken for the above-mentioned problems from a longer-term perspective, it is necessary to explore the possibility of inexpensive biopharmaceuticals such as short-chain peptides in the future in addition to the pursuit of a superior drug seed.

Fukuda, one of the present inventors, hosted a laboratory in Sanford Burnham Prebys Medical Discovery Institute in the United States for more than 30 years until she was assigned to the National Institute of Advanced Industrial Science and Technology in 2014. During that time, Fukuda succeeded for the first time in the world in inhibiting sugar chain-dependent cancer metastasis by using a peptide mimicking the structure of sugar chain (non-patent document 1). Furthermore, in the process of examining vascular endothelial receptors interacting with these sugar chain mimetic peptides, she found that a peptide named IF7 binds to annexin A1 (Anxa1) (non-patent document 2). Anxa1 was clarified by the group of Jan Schnitzer et al. to be the most specific of the currently known tumor vessel specific marker molecules and is expressed intracellularly in normal cells but strongly expressed on luminal surfaces adjacent to the bloodstream in tumor neovascular endothelial cells (non-patent document 3). Fukuda et al. clarified that a drug (IF7-SN38) obtained by binding an anticancer agent (SN38) to IF7 clears tumor in cancer-bearing mice at a low dose (non-patent document 2). While IF7 binds to the N-terminal region of mouse Anxa1, the amino acid sequence in that region is highly conserved between mouse and human. Therefore, IF7-SN38 may also be useful in human. This finding was taken up in the "In this issue in PNAS" of the PNAS journal and the NIH introduced a special article. The finding further attracted considerable attention, including reports by media around the world.

DOCUMENT LIST

Non-Patent Documents non-patent document 1: Fukuda et al., Cancer Research, 60: 450-6, 2000
non-patent document 2: Hatakeyama et al., Proc. Natl. Acad. Sci USA, 108: 19587-92, 2011
non-patent document 3: Oh et al., Nature 429: 629-35, 2004

SUMMARY OF THE INVENTION

Problems to be Solved by the Invention

When IF7 is administered intravenously to cancer-bearing mice, it reaches the blood vessels surrounding the tumor, after which IF7 is taken up into vesicles from the luminal side of vascular endothelial cells and moves to the basal side, where it is released into the stroma where cancer cells are present. Also in mouse vascular endothelial F2 cells, IF7 bound to Anxa1 actively traversed tumor vascular endothelial cells by transcytosis. Therefore, it was suggested that IF7 has an activity to cross the blood vessel-brain tumor barrier in the brain tumor. Surprisingly, intravenous injection of fluorescent-labeled IF7 into brain tumor model mice transplanted with glioma cells resulted in accumulation of fluorescence at a high concentration in the tumor site in the brain. Fluorescence also crossed blood vessels and reached cancer cells in the brain stroma. Furthermore, subcutaneous tumor and brain tumor were created in the same mouse (dual tumor model), and the therapeutic effect of IF7-SN38 was tested. As a result, both brain tumor and subcutaneous tumor were suppressed, and the effect thereof was higher in the brain tumor than in the subcutaneous tumor. Similar results were obtained in B16 melanoma metastatic brain tumor model, and the results remained same even when the host mouse was changed to C57BL/6 or SCID strain. These facts indicate that DDS targeting Anxa1 not only efficiently cross the blood-brain tumor barrier but also provide excellent therapeutic effects in brain tumor.

As described above, while IF7 has an excellent malignancy targeting activity, it has two problems for clinical development: low solubility and low stability. First, IF7 peptide is protease sensitive and easily degraded. In fact, in an experiment including intravenous administration of A488-IF7 to healthy mice, the fluorescence signal of the peripheral blood almost disappeared in about 1 hour. However, by tail vein administration to cancer-bearing mice, fluorescence of A488-IF7 recovered from the peripheral blood was significantly less than in healthy mice. This result suggests that most of A488-IF7 accumulates rapidly in the tumor while undergoing degradation. Also, IF7 is highly hydrophobic and causes difficulty in dosage form, for example, when a compound bound with an anticancer agent is administered intravenously, a surfactant needs to be added to avoid precipitation after dissolution in DMSO.

Therefore, it is an object of the present invention to provide a novel peptide that binds to annexin A1 and use thereof capable of at least partially overcoming the above-mentioned problems associated with IF7.

Means of Solving the Problems

To solve the above-mentioned problems, the present inventors conducted intensive studies and had an idea of exploring a D-form peptide capable of binding to annexin A1. To this end, the present inventors synthesized a D-form peptide (D-MC16) in mirror image relation with 16-residue L-form peptide (L-MC16) having a modifying Cys residue added to the N-terminal 15 residues of Anxa1 known to bind to IF7, and screened using a T7 phage library to identify a plurality of 7-amino acid L-form peptides that bind to D-MC16. They conducted further studies of a peptide called TIT7 peptide, which was particularly promising among the identified L-form peptides. As the inventors predicted, they confirmed that the D-form peptide (dTIT7 peptide), which is in mirror image relation with the TIT7 peptide, binds to Anxa1. Furthermore, the present inventors have demonstrated by in vivo experiments that dTIT7 peptides accumulate in the tumor site when administered to brain tumor model mice via the tail vein, that dTIT7 peptide (GA-dTIT7) bound with an anticancer agent (geldanamycin) markedly inhibited tumor growth when intravenously administered to cancer-bearing mice, thus causing massive necrosis in the tumor site, and that oral administration of GA-dTIT7 suppressed tumor growth in both brain tumor model mice transplanted with C6 cells into the brain and brain metastasis model mice transplanted with B16 cells into the brain, the tumor continued to reduce even after cessation of drug administration, and complete cure was finally achieved in some animals.

The present inventors have conducted further studies based on the above results, and have completed the present invention. The present invention is as follows.

[1] A peptide comprising the amino acid sequence of any of the formulas (I)-(III) below:
(I) an amino acid sequence of (X1)[D]P[D](X2)[D] wherein X1 is W or F, X2 is S or T, and each amino acid symbol immediately followed by symbol [D] is a D form of the amino acid,
(II) an amino acid sequence of P[D]T[D](X)$_n$ F[D] wherein (X)$_n$ is any amino acid in the number of n selected independently of each other, n is an integer of 0-4, and the symbol [D] is as defined above,
(III) an amino acid sequence that is a Retro-inverso of the amino acid sequence of any of the aforementioned (I) and the aforementioned (II).

[2] A peptide comprising the amino acid sequence of any of the following (i)-(vii) (in the following sequences, symbol [D] is as defined above):
(i) an amino acid sequence of T[D] I[D] T[D] W[D] P[D] T[D] M[D],
(ii) an amino acid sequence of L[D] R[D] F[D] P[D] T[D] V[D] L[D],
(iii) an amino acid sequence of L[D] L[D] S[D] W[D] P[D] S[D] A[D],
(iv) an amino acid sequence of S[D] P[D] T[D] S[D] L[D] L[D] F[D],
(v) an amino acid sequence of M[D] P[D] T[D] L[D] T[D] F[D] R[D],
(vi) an amino acid sequence of any of the aforementioned (i)-(v), in which 1 or several amino acids are inserted, substituted or deleted, or these are combined,
(vii) an amino acid sequence that is a Retro-inverso of the amino acid sequence of any of the aforementioned (i)-(vi).

[3] The peptide of [2], comprising the amino acid sequence of the above-mentioned (i).

[4] The peptide of [2], consisting of the amino acid sequence of the above-mentioned (i).

[5] A conjugate comprising the peptide of any of [1] to [4], and one or more components.

[6] The conjugate of [5], wherein the one or more components comprise an anticancer agent.

[7] The conjugate of [6], wherein the above-mentioned anticancer agent is selected from the group consisting of an antimetabolite, an alkylating agent, an anticancer antibiotic, a microtubule inhibitor, a platinum preparation, a topoisomerase inhibitor, a molecular targeting agent, and an anti-angiogenic agent.

[8] The conjugate of [6] or [7], which is selected from the group consisting of enocitabine, capecitabine, carmofour, cladribine, gemcitabine, cytarabine, cytarabine ocfosfate, tegafur, tegafur/uracil, tegafur/gimeracil/oteracil potassium, doxifluridine, nelarabine, hydroxycarbamide, fluorouracil, fludarabine, pemetrexed, pentostatin, mercaptopurine, methotrexate; cyclophosphamide, ifosfamide, melphalan, busulfan, thiotepa, nimustine, ranimustine, dacarbazine, procarbazine, temozolomide, carmustine, streptozotocin, bendamustine; actinomycin D, aclarubicin, amrubicin, idarubicin, epirubicin, zinostatin stimalamer, daunorubicin, doxorubicin, pirarubicin, bleomycin, peplomycin, mitomycin C, mitoxantrone, liposomal doxorubicin;
vinblastine, vincristine, vindesine, paclitaxel, docetaxel, oxaliplatin, carboplatin, cisplatin, nedaplatin;
camptothecin, irinotecan, nogitecan, SN-38, doxorubicin, etoposide, levofloxacin, ciprofloxacin;
legolafenib, cetuximab, panitumumab, ramsilmab, gefitinib, erlotinib, afatinib, crizotinib, alectinib, ceritinib, libertinib, trastuzumab, lapatinib, pertuzumab, sunitinib, sorafenib, axitinib, pazopanib, nivolumab, pembrolizumab, ipilimumab, vemurafenib, everolimus, temsirolimus, rituximab, bevacizumab, geldanamycin;
angiostatin, endostatin, metastatin, anti-VEGF antibody and VEGFR-2 inhibitor.

[9] The conjugate of [5], wherein the one or more components comprise a detectable substance.

[10] The conjugate of [9], wherein the detectable substance enables detection of the conjugate in vivo by a means selected from the group consisting of X-ray photography, computed tomography (CT), nuclear magnetic resonance imaging (MRI), ultrasonography, scintigraphy, positron emission tomography (PET), endoscopy and laparoscopy.

[11] The conjugate of [9] or [10], wherein the detectable substance is a radioisotope, an MRI enhancer, a radiopaque substance, a contrast agent or a fluorescent substance.

[12] The conjugate of any of [9] to [11], wherein the detectable substance is selected from the group consisting of a radioactive nuclide selected from $^{18}F$, $^{51}Mn$, $^{52m}Mn$, $^{52}Fe$, $^{55}Co$, $^{62}Cu$, $^{64}Cu$, $^{68}Ga$, $^{72}As$, $^{75}Br$, $^{76}Br$, $^{82m}Rb$, $^{83}Sr$, $^{86}Y$, $^{89}Zr$, $^{94m}Tc$, $^{110}In$, $^{120}I$, $^{124}I$ and the like. Examples of the radioactive nuclide useful for detection of γ ray include $^{51}Cr$, $^{57}Co$, $^{58}Co$, $^{59}Fe$, $^{67}Cu$, $^{67}Ga$, $^{75}Se$, $^{97}Ru$, $^{99m}Tc$, $^{111}In$, $^{114m}In$, $^{123}I$, $^{125}I$, $^{131}I$, $^{169}Yb$, $^{197}Hg$ and $^{201}Tl$;

a paramagnetic ion selected from chromium (III), manganese (II), iron(II), cobalt(II), nickel(II), copper(II), neodymium (III), samarium (III), ytterbium (III), gadolinium (III), vanadium (II), terbium (III), dysprosium (III), holmium (III) and erbium (III), lanthanum (III), gold lead (II), bismuth (III);

an iodine compound, a barium compound, a gallium compound, a thallium compound;

rhodamine, fluorescein, Cy dye, Alexa (registered trademark) Fluor, phycoerythrin (PE), allophycocyanin (APC), derivatives thereof and a near infrared fluorescent reagent.

[13] A composition comprising the peptide of any of [1] to [4] or the conjugate of any of [5] to [12], and a pharmacologically acceptable carrier.

[14] A composition for the treatment of cancer, comprising the conjugate of any of [6] to [8], and a pharmacologically acceptable carrier.

[15] A composition for testing for cancer, comprising the conjugate of any of [9] to [12], and a pharmacologically acceptable carrier.

[16] The composition of [14] or [15], wherein the cancer is a solid cancer or a liquid cancer.

[17] The composition of [16], wherein the solid cancer is an angiogenic solid cancer.

[18] The composition of [16] or [17], wherein the solid cancer is cancer of the brain or nervous system, cancer of the head and neck, cancer of the digestive tract, cancer of the urinary or reproductive organ, cancer of the respiratory system, cancer of the breast, cancer of the skin, cancer of the bone, or cancer of the muscle.

[19] The composition of any of [16] to [18], wherein the solid cancer is brain tumor, spinal cord tumor, laryngeal cancer, oral cancer, salivary gland cancer, paranasal sinus cancer, thyroid cancer, stomach cancer, esophageal cancer, small intestine cancer, colon cancer, rectal cancer, anal cancer, liver cancer, biliary tract cancer, pancreatic cancer, kidney cancer, kidney cell cancer, bladder cancer, prostate cancer, renal pelvis and ureter cancer, gall bladder cancer, bile duct cancer, testis cancer, penile cancer, uterine cancer, endometrial cancer, uterine sarcoma, cervical cancer, vaginal cancer, vulvar cancer, ovarian cancer, fallopian tube cancer, lung cancer, breast cancer, malignant melanoma, osteosarcoma or rhabdomyosarcoma.

[20] The composition of [19], wherein the solid cancer is a benign or malignant brain tumor.

[21] The composition of [20], wherein the brain tumor is a primary brain tumor or a metastatic brain tumor.

[22] The composition of [20] or [21], wherein the brain tumor is meningioma, pituitary adenoma, schwannoma, astrocytoma, oligodendroglioma, anaplastic astrocytoma, anaplastic oligodendroglioma, anaplastic oligoastrocytoma or glioblastoma.

[23] The composition of [16], wherein the liquid cancer is B-cell lymphoma.

Effect of the Invention

According to the present invention, a novel peptide that binds to annexin A1 is provided.

As evident in the case of erythropoietin and recent anti-PD-1 antibodies, clinically successful pharmaceuticals have a very high specificity of expression of the biomolecule targeted by drugs. Since annexin A1 targeted by the peptide of the present invention is the most specific molecule among the currently known neovascular target markers of malignant tumor, an anticancer agent in which the peptide of the present invention is combined may exhibit a superior therapeutic effect compared to the existing anticancer agents.

In particular, the peptide-anticancer agent conjugate is not only capable of accumulating an anticancer agent in malignant tumor with high efficiency but is also protease resistant, thus allowing for a reduction in the number of effective doses and even lower doses. In addition, complete cure of the malignant tumor may be expected by the combined use of an anticancer agent and immunotherapy, since the immune system is considered to be preserved.

The characteristic feature of annexin A1 is that it is expressed on the blood side of neovascular endothelial cell formed in a tumor, and when bound on the blood side with a ligand such as the peptide of the present invention, the ligand is transported to the basal side by transcytosis and is actively released into the stroma where cancer cells are present. This property may also serve as a mechanism to actively cross the vascular brain barrier. The peptide of the present invention targeting annexin A1, unlike conventional angiogenesis inhibitors (Avastin) and temozolomide (described above), allows the treatment of malignant brain tumor by an innovative mechanism. That is, currently, chemotherapeutic agents that cross the blood-brain barrier, that accumulate in tumor tissue, and that can be stable in the body and administered orally have been developed, but a chemotherapeutic agent combining all of them does not exist except the peptide of the present invention (FIG. 10).

Since the peptide of the present invention can be combined with various anticancer agents, it can afford a wide range of physiological activity.

The present invention opens a breakthrough for the treatment of brain tumors. In addition, ANXA1 is known to be expressed on vascular surfaces of various malignant tumors, and a dTIT7-bound anticancer agent is expected to be clinically applicable as a therapeutic agent for not only brain tumor but also a wide range of cancers.

In addition, since the peptide of the present invention permits easy chemical synthesis and modification, it is highly promising as a middle molecular biopharmaceutical replacing the antibody pharmaceuticals. In particular, since the peptide of the present invention can be a short chain peptide (e.g., 7 residues of amino acids), it can be produced economically by chemical synthesis.

Furthermore, the peptide of the present invention and a conjugate containing the peptide and other functional part have excellent stability and can also be used as pharmaceuticals for oral administration. Clinical trials are therefore also easy. After actually approved as a medical drug, it can be spread as a pharmaceutical even in the underdeveloped countries where medical facilities are scarce.

In addition, a conjugate containing the peptide of the present invention and a detectable substance is useful in, for example, cancer diagnostic applications. The present inventors attempted PET testing of mice using IF7 in the past, but no tumor-specific images were obtained. The reason for the failure is considered to be that IF7 bound to a radioactive reagent was buried inside the compound due to the high hydrophobicity of IF7. The peptide of the present invention can be water soluble and thus can overcome this problem. The peptide of the present invention permits relatively easy modification of, for example, the N-terminal, can labeled with reagents for 3D imaging such as PET, and can be developed as a diagnostic agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

1. Peptide

Figure 1:
FIG. 1 shows a brain tumor targeting effect of IF7. Brain tissue sections after intravenous administration of IF7-A488 to brain tumor model mice. A488 (left) and Hoechst (right, tumor site). RQ7 is an inverse sequence negative control of IF7. Bars; 5 mm.

The present invention provides a peptide containing the amino acid sequence of any of (I)-(III) below.

(I) an amino acid sequence of (X1)[D]P[D](X2)[D] wherein X1 is W or F, X2 is S or T, (II) an amino acid sequence of P[D]T[D](X)$_n$ F[D] wherein (X)$_n$ is any amino acid in the number of n selected independently of each other, n is an integer of 0-4, (III) an amino acid sequence that is a Retro-inverso of the amino acid sequence of any of the aforementioned (I) and the aforementioned (II).

The present invention also provides a peptide containing the amino acid sequence of any of the following (i)-(vii):

(i) an amino acid sequence of T[D] I[D] T[D] W[D] P[D] T[D] M[D],
(ii) an amino acid sequence of L[D] R[D] F[D] P[D] T[D] V[D] L[D],
(iii) an amino acid sequence of L[D] L[D] S[D] W[D] P[D] S[D] A[D],
(iv) an amino acid sequence of S[D] P[D] T[D] S[D] L[D] L[D] F[D],
(v) an amino acid sequence of M[D] P[D] T[D] L[D] T[D] F[D] R[D],
(vi) an amino acid sequence of any of the aforementioned (i)-(v), in which 1 or several amino acids are inserted, substituted or deleted, or these are combined,
(vii) an amino acid sequence that is a Retro-inverso of the amino acid sequence of any of the aforementioned (i)-(vi).

In the present specification, the amino acid sequence of the chain peptide is described according to the conventional manner of peptide indication with the N-terminal side on the left side and the C-terminal side on the right side. In addition, each amino acid symbol with symbol [D] immediately following the amino acid sequence indicates a D form of the amino acid, and each amino acid symbol without symbol [D] immediately following the amino acid sequence indicates an L form of the amino acid, unless contrary to the context. In the present specification, a peptide containing the amino acid sequence of any one of the above-mentioned (I)-(II) and a peptide containing the amino acid sequence of any one of the above-mentioned (i)-(vii) are collectively referred to as the peptide of the present invention.

The amino acid sequence of the above-mentioned (I) may be any of W[D] P[D] S[D], W[D] P[D] T[D], F[D] P[D] S[D] and F[D] P[D] T[D].

In the amino acid sequence of the above-mentioned (II), the integer n is 0 to 4, preferably 2 to 3. X may be any amino acid selected independently of each other.

The peptide of the present invention may consist of the amino acid sequence of any of the above-mentioned (I)-(III) and (i)-(vii), or may have one or more amino acids added to the N-terminal side and/or C-terminal side of these sequences.

In the present specification, the peptide refers to one in which two or more amino acids are peptide-bonded. The length of the peptide of the present invention is not particularly limited. The peptide of the present invention may contain at least 3, at least 4, at least 5, at least 6, at least 7, at least 8, at least 9, at least 10, at least 11, at least 12, at least 13, at least 14 or at least 15 amino acids. The peptide of the present invention may consist of up to 50, 45, 40, 35, 30, 25, 20, 19, 18, 17, 16, 15, 14, 13, 12, 11, 10, 9, 8 or 7 amino acids. The peptide of the present invention may have a length of 3-10, 3-15, 3-20, 3-25, 3-30, 3-40, 3-50, 4-10, 4-15, 4-20, 4-25, 4-30, 4-40, 4-50, 5-10, 5-15, 5-20, 5-25, 5-30, 5-40, 5-50, 6-10, 6-15, 6-20, 6-25, 6-30, 6-40, 6-50, 7-10, 7-15, 7-20, 7-25, 7-30, 7-40, 7-50, 8-10, 8-15, 8-20, 8-25, 8-30, 8-40 or 8-50 amino acids. For example, the peptide of the present invention may have a length of 3, 4, 5, 6, 7, 8, 9, 10, 11, 12, 13, 14 or 15 amino acids.

The peptide of the present invention may be composed of a combination of a form D amino acid and a form L amino acid. In more detail, all the amino acids constituting the peptide containing the amino acid sequence of any of the above-mentioned (I)-(II) and (i)-(vi) may be form D amino acids, may contain form L amino acid in addition to form D amino acids, and all the amino acids constituting the peptide containing the amino acid sequence of the above-mentioned (III) or (vii) may be form L amino acids, or may contain form D amino acid in addition to form L amino acids. The L-form amino acid may be a naturally occurring L-form amino acid and examples include glycine, alanine, leucine, proline, phenylalanine, tyrosine, methionine, serine, threonine, cysteine, aspartic acid, glutamic acid, asparagine, glutamine, lysine, arginine, hydroxylysine, histidine, tryptophan, valine, all of which are in the L form. The D-form amino acid includes, for example, an optical isomer of an L-form amino acid as described above. In the present specification, glycine, which is an amino acid that does not exhibit optical activity, can be read as an L-form and D-form amino acid unless contrary to the context.

The peptide of the present invention may contain a modified or unusual amino acid such as those referred to under 37 C.F.R. 1.821-1.822 and the like. In one embodiment, the peptide of the present invention does not contain a modified or unusual amino acid. Examples of the modified or unusual amino acid include 3-aminoadipic acid, β-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, 6-N-methyllysine, N-methylvaline, norvaline, norleucine, ornithine and the like.

The amino terminal and/or carboxy terminal of the peptide of the present invention may be modified. The modification of the amino terminal may be methylation (e.g., —NHCH$_3$ or —N(CH$_3$)$_2$), acetylation (e.g., by acetic acid or its halogenated derivative thereof), or any protecting group such as benzyloxycarbonyl group, carboxylate functional group (RCOO—) or sulfonyl functional group (R—SO$_2$—) (wherein R is selected from alkyl, aryl, heteroaryl, and alkylaryl, and the like may be introduced. Modification of the carboxy terminal include amidation (—CONH$_2$), esterification (—COOR) and the like. Here, as R in the ester, for example, a C$_{1-6}$ alkyl group such as methyl, ethyl, n-propyl, isopropyl; n-butyl; a C$_{3-8}$ cycloalkyl group such as cyclopentyl, cyclohexyl; a C$_{6-12}$ aryl group such as phenyl, α-naphthyl; a phenyl-C$_{1-2}$ alkyl group such as benzyl, phenethyl; a C$_{7-14}$ aralkyl group such as α-naphthyl-C$_{1-2}$ alkyl group; a pivaloyloxymethyl group and the like are used.

The peptide of the present invention may undergo various modifications other than that at the N-terminal or C-terminal. Chemical modification may be, for example, methylation, acetylation, phosphorylation, and the like. When the peptide of the present invention has a carboxyl group (or carboxylate) at a site other than the C-terminal, the carboxyl group may be amidated or esterified. As the ester in this case, for example, the C-terminal ester described above and the like are used. Alternatively, the substituents on the side chain of the amino acid in a molecule (e.g., —OH, —SH, amino group, imidazole group, indole group, guanidino group, etc.) may be protected with an appropriate protecting group (e.g., C$_{1-6}$ acyl group such as C$_{1-6}$ alkanoyl group such as formyl, acetyl, etc.).

The peptide of the present invention containing the amino acid sequence of the above-mentioned (vi) may contain a partial sequence consisting of four consecutive amino acids, a partial sequence consisting of five consecutive amino acids, or a partial sequence consisting of six consecutive amino acids in the amino acid sequence of the above-mentioned (i)-(v). To be specific, for example, when the original amino acid sequence is the amino acid sequence of the above-mentioned (i), the peptide may contain the amino acid sequence of T[D] I[D] T[D] W[D], the amino acid sequence of I[D] T[D] W[D] P[D], the amino acid sequence of T[D] W[D] P[D] T[D], the amino acid sequence of W[D] P[D] T[D] M[D], the amino acid sequence of T[D] I[D] T[D] W[D] P[D], the amino acid sequence of I[D] T[D] W[D] P[D] T[D], the amino acid sequence of T[D] W[D] P[D] T[D] M[D], the amino acid sequence of T[D] I[D] T[D] W[D] P[D] T[D] or the amino acid sequence of I[D] T[D] W[D] P[D] T[D] M[D].

The position of mutation (i.e., insertion, substitution, deletion, and combination thereof) in the amino acid sequence of the above-mentioned (vi) is not particularly limited. The mutation may consist of (a) insertion only, (b) substitution only, (c) deletion only, (d) insertion and substitution only, (e) insertion and deletion only, (f) substitution and deletion only, or (g) a combination of insertion, substitution and deletion. The number of mutation in the above-mentioned (a)-(g) is, for example, 1-5, preferably 1-4, more preferably 1-3, further more preferably 1 or 2, even more preferably 1.

The amino acid inserted in the amino acid sequence of the above-mentioned (vi) may be any amino acid described above. The amino acid may be an L-form or D-form amino acid, for example, a naturally occurring L-form amino acid described above, or a D-form amino acid which is an optical isomer thereof. The amino acid may also undergo various chemical modifications described above.

Preferably, the substitution in the amino acid sequence of the above-mentioned (vi) is a conservative amino acid substitution. The "conservative amino acid substitution" is well known in the art. For example, conservative amino acid substitution can be defined as substitution between amino acids having similar properties of the side chain. Thus, the conservative amino acid substitution may be, for example, (1) substitution between aromatic amino acids (Phe, Trp, Tyr), (2) substitution between non-polar aliphatic amino acids (Gly, Ala, Val, Leu, Met, Ile, Pro), (3) substitution between non-charged polar amino acids (Ser, Thr, Cys, Asn, Gln), (4) substitution between basic amino acids (Lys, Arg, His), or (5) substitution between acidic amino acids (Asp, Glu). In the present specification, the conservative amino acid substitution may also include substitution of a form D amino acid with a form L amino acid which is an optical isomer thereof. Thus, the conservative amino acid substitution may also be substitution between two L-form amino acids, substitution between two D-form amino acids, or substitution between an L-form amino acid and a D-form amino acid within the groups of the above-mentioned (1)-(5).

In one embodiment, the sequence of the above-mentioned (vi) may be encompassed in the sequence of the above-mentioned (I) or (II). In this case, the sequence of the above-mentioned (vii) is encompassed in the sequence of the above-mentioned (III). In such embodiments, the fourth amino acid may be W[D] or F[D] and the fifth amino acid may be P[D] and the sixth amino acid may be T[D] or S[D] in the sequence of the above-mentioned (i), the third amino acid may be W[D] or F[D] and the fourth amino acid may be P[D] and the fifth amino acid may be T[D] or S[D] in the sequence of the above-mentioned (ii), the fourth amino acid may be W[D] or F[D] and the fifth amino acid may be P[D] and the sixth amino acid may be T[D] or S[D] in the sequence of the above-mentioned (iii), the second amino acid may be P[D] and the third amino acid may be T[D] and the sixth amino acid may be F[D] in the sequence of the above-mentioned (iv), and, the second amino acid may be P[D] and the third amino acid may be T[D] and the fifth amino acid may be F[D] in the sequence of the above-mentioned (v).

Retro-inverso isomer of peptide refers to a peptide in which the chirality of each amino acid residue is reversed ("inverso") and the direction of the amino acid sequence is reversed ("Retro") relative to the original peptide. Retro-inverso isomer is known to exhibit a structure and function similar to those of the original peptide (e.g., Acc. Chem. Res., 1993, 26(5), pp 266 273, and PLoS One. 20.13 Dec. 2; 8(12):e80390). Specifically, the amino acid sequence of the above-mentioned (vii) includes, for example, MTPWTIT (SEQ ID NO: 1) which is the Retro-inverso of the sequence of the above-mentioned (i), LVTPFRL (SEQ ID NO: 2) which is the Retro-inverso of the sequence of the above-mentioned (ii), ASPWSLL (SEQ ID NO: 3) which is the Retro-inverso of the sequence of the above-mentioned (iii), FLLSTPS (SEQ ID NO: 4) which is the Retro-inverso of the sequence of the above-mentioned (iv), and RFTLTPM (SEQ ID NO: 5) which is the Retro-inverso of the sequence of the above-mentioned (v).

The peptide of the present invention may contain two or more sequences selected from the above-mentioned (I)-(III) and (i)-(vii). In one embodiment, the peptide of the present invention contains a tandem repeat of any of the sequences of the above-mentioned (I)-(III) and (i)-(vii) (i.e., a structure in which identical sequence portions are directly linked to each other). In another embodiment, the peptide of the present invention contains a structure in which two or more different sequences of the above-mentioned (I)-(III) and (i)-(vii) are directly linked. Specific repeat structures include, for example, T[D]I[D]T[D]W[D]P[D]T[D]M[D]-T[D]I[D]T[D]E[D]P[D]T[D]M[D], and T[D]I[D]T[D]-T[D]I[D]T[D]. Alternatively, the peptide of the present invention may constitute a multivalent peptide with a dendrimer.

The peptide of the present invention may be a free form or a salt form. Examples of the salt of the peptide of the present invention include a pharmaceutically acceptable acid addition salt and a base addition salt. Examples of the acid addition salt include salts with inorganic acids such as hydrochloric acid, sulfuric acid, nitric acid, phosphoric acid and the like, and salts with organic acids such as acetic acid, malic acid, succinic acid, tartaric acid, citric acid and the like. Examples of the base addition salt include salts with alkali metals such as sodium, potassium and the like, salts with alkaline earth metals such as calcium, magnesium and the like, and salts with amines such as ammonium, triethylamine and the like.

The peptide of the present invention may bind to annexin A1. Annexin A1 (Anxa1) is a known protein belonging to the annexin family, also known as lipocortin 1. Genetic sequence and amino acid sequence of Anxa1 are known for various species. For example, RefSeq No. NM-000700.2 (SEQ ID NO: 6) of mRNA, RefSeq No. NP-000691.1 (SEQ ID NO: 7) of protein for human Anxa1; RefSeq No. NM-010730.2 (SEQ ID NO: 8) of mRNA, RefSeq No. NP-034860.2 [ARRAY ID NO:9] of protein for mouse Anxa1 can be mentioned. The peptide of the present invention may bind to the N-terminal region of Anxa1. More particularly, the peptide of the present invention may bind to a region consisting of 1st to 15th amino acids of SEQ ID NO: 7 in human Anxa1 or a region consisting of 1st to 15th amino acids of SEQ ID NO: 9 in murine Anxa1. The peptide of the present invention may have dissociative constant (Kd value) of preferably less than $10^{-6}$ M, more preferably less than $10^{-7}$ M, further more preferably less than $5\times10^{-8}$ M when, for example, intermolecular interactions with mouse or human Anxa1 are measured using the QCM (Quartz Crystal Microbalance) method. For the above-mentioned measurement, human recombinant Anxa1 protein consisting of 346 amino acid residues, which is commercially available from ATGen Corporation (Seongnam-si, South Korea) can be used.

The peptide of the present invention can be produced according to a known peptide synthesis method. The method of peptide synthesis may be any of, for example, a solid phase synthesis process and a liquid phase synthesis process. The object peptide can be produced by condensing a partial peptide or amino acid capable of constituting the peptide of the present invention and the remaining portion and, when the product has a protecting group, by eliminating the protecting group.

Here, the condensation and elimination of a protecting group can be performed according to a method known per se, for example, the methods described in the following (1)-(8).
(1) M. Bodanszky & M. A. Ondetti, Peptide Synthesis, Interscience Publishers, New York (1966)
(2) Schroeder & Luebke, The Peptide, Academic Press, New York (1965)
(3) Nobuo Izumiya, et al.: Peptide Gosei-no-Kiso to Jikken (Basics and experiments of peptide synthesis), published by Maruzen Co. (1975)
(4) Haruaki Yajima and Shunpei Sakakibara: Seikagaku Jikken Koza (Biochemical Experiment) 1, Tanpakushitsu no Kagaku (Chemistry of Proteins) IV, 205 (1977)
(5) Haruaki Yajima, ed.: Zoku Iyakuhin no Kaihatsu (A sequel to Development of Pharmaceuticals), Vol. 14, Peptide Synthesis, published by Hirokawa Shoten.
(6) Stewart, J. M. & Young, J. D., "Solid phase peptide synthesis (2nd ed.)", Pierce Chemical Company, Rockford (1984)
(7) Atherton, E. & Sheppard, R. C., "Solid Phase peptide synthesis: a practical approach", IRL Press, Oxford (1989)
(8) "Fmoc Solid Phase Peptide Synthesis: A Practical Approach (Practical Approach Series)", Oxford University Press (2000)

The thus-obtained peptide can be purified and isolated by a known purification method. Examples of the purification method include solvent extraction, distillation, column chromatography, liquid chromatography, recrystallization, combinations thereof and the like.

When the peptide obtained by the above-mentioned method is in a free form, the form can be converted to a suitable salt by a known method or a method analogous thereto; conversely, when the peptide is obtained in the form of a salt, the salt can be converted to a free form or other salt by a known method or a method analogous thereto.

As stated above, annexin A1 is known to have the highest specificity among the currently known tumor vessel specific marker molecules, and is expressed intracellularly in normal cells, but strongly expressed on luminal surface adjacent to the blood stream in tumor neovascular endothelial cells (Oh et al., Nature 429: 629-35, 2004). Thus, the peptide of the present invention can selectively bind to angiogenic tumors in vivo. In addition, Anxa1 is expressed on the blood side of neovascular endothelial cells formed in tumors, and when bound on the blood side to ligands such as the present peptides, the ligands are transported to the basal side by transcytosis and are actively released into the stroma where cancerous cells are present. Thus, the peptide of the present invention can target malignancies in vivo. Thus, the peptide of the present invention is useful, for example, for targeting malignant tumors.

2. Conjugate

The present invention also provides a conjugate in which one or more components are bound with the above-mentioned peptide of the present invention (hereinafter to be also referred to as the conjugate of the present invention).

The component is not particularly limited as long as it can be linked to the peptide of the present invention, and may be suitable for administration to an animal (e.g., human), and may perform some function in the body of the animal. The component may be natural or non-natural. Examples of the component include, but are not limited to, biological materials (e.g., cell, phage, virus, etc.), oligonucleotides and nucleic acids (e.g., DNA, RNA, DNA/RNA chimera, etc.), peptide, polypeptide, protein, antibody, lipid, polysaccharide, small molecule compounds (e.g., organic or inorganic compounds of not more than 1000 Da), particles (e.g., gold particles, various nanoparticles, etc.), combinations thereof, and the like.

The component may perform a given functionality at a target site in the body of an animal (e.g., human). The type of the functionality is not particularly limited. Since the conjugate of the present invention can be targeted to malignant tumor by the action of the part corresponding to the peptide of the present invention, preferred examples of the functionality include anti-cancer activity and provision of detectability. Thus, the component may be, for example, an anticancer agent or a detectable substance.

(Anticancer Agent)

In the present specification, the anticancer agent refers to a drug intended to suppress growth of a malignant tumor (cancer). The mechanism of the action of anticancer agent is not particularly limited. The anticancer agent may be an antimetabolite, an alkylating agent, an anticancer antibiotic, a microtubule inhibitor, a platinum preparation, a topoisomerase inhibitor, a molecular targeting agent, or the like. The conjugate of the present invention may contain two or more the same or different anticancer agents.

The metabolic antagonist may be, for example, a folic acid antimetabolite, a dihydropteroate synthase inhibitor, a dihydrofolate reductase inhibitor (DHFR inhibitor), a pyrimidine metabolism inhibitor, a thymidylate synthase inhibitor, a purine metabolism inhibitor, an IMPDH inhibitor, a ribonucleotide reductase inhibitor, a ribonucleotide reductase inhibitor, a nucleotide analog, L-asparaginase and the like. Specific examples of the metabolic antagonist include enocitabine (SUNRABIN), capecitabine (Xeloda), carmofour (Mifurol), cladribine (Leustatin), gemcitabine (Gemzar), cytarabine (kiloside), cytarabine ocfosfate (Starasid), tegafur (Achillon, AFTHOUR, Tefseal, Futrafur, Lunasin etc.), tegafur/uracil (UFT), tegafur/gimeracil/oteracil potassium (TS-1: T-S-One), doxifluridine (FURTURON), nelarabine (Arranon G), hydroxycarbamide (HYDREA), fluorouracil (5-FU, carzonal, Benton, Lunachol, Lunapon), fludarabine (fludara), pemetrexed (alimta), pentostatin (cofolin), mercaptopurine (leukerin), methotrexate (methotrexate) and the like.

Specific examples of the alkylating agent include nitrogen mustard based alkylating agents such as cyclophosphamide (endoxane), Ifosfamide (ifomide), melphalan (alkeran), busulfan, thiotepa (tespamine) and the like, nitrosourea-based alkylating agents such as nimustine (nidran), ranimustine (cymerin), dacarbazine (dacarbazine), procarbazine (procarbazine hydrochloride), temozolomide (Temodal), carmustine (Gliadel), streptozotocin (zanosar), bendamustine (treakisym) and the like.

Specific examples of the anti-cancer antibiotic include actinomycin D (cosmegen), aclarubicin (aclacinone), amrubicin (Calsed), idarubicin (idamycin), epirubicin (epirubicin hydrochloride, Farmorubicin), zinostatin stimalamer (Smancs), daunorubicin (daunomycin), doxorubicin (adriacin), pirarubicin (Pinorubin, THERARUBICIN), bleomycin (Bleo), peplomycin (Peleo), mitomycin C (Mitomycin), mitoxantrone (Novantrum), liposomal doxorubicin (Doxil) and the like.

Examples of the microtubule inhibitor include vinca alkaloid microtubule polymerization inhibitors such as vinblastine (exal), vincristine (oncovin), vindesine (Fildesin) and the like, taxane type microtubule depolymerization inhibitors such as paclitaxel (taxol), docetaxel (taxotere) and the like.

Examples of the platinum preparation include oxaliplatin (El Prat), carboplatin (Carboplatin, Carbomerck, Paraplatin), cisplatin (IA-call, Konaburi, Cisplatin etc.), nedaplatin (Aqupla) and the like.

Examples of the topoisomerase inhibitor include type I topoisomerase inhibitors such as camptothecin and a derivative thereof (e.g., irinotecan (Campto), nogitecan (HYCAMTIN), SN-38 and the like) and the like; type II topoisomerase inhibitors such as anthracycline drugs such as doxorubicin (adriacin) and the like, epipodophyllotoxin drugs such as etoposide (Lastet, VePesid) and the like, and quinolone drugs such as levofloxacin (cravit), ciprofloxacin (ciproxan) and the like.

Examples of the molecular target drug include legolafenib (Stivarga), cetuximab (Erbitux), panitumumab (Vectibix), ramsilmab (Cyramza), gefitinib (Iressa), erlotinib (Tarceva), afatinib (GIOTRIF), crizotinib (XALKORI), alectinib (ALECENSA), ceritinib, Lenvatinib (Lenvima), trastuzumab (Herceptin), lapatinib (Tykerb), pertuzumab (PERJETA), sunitinib (Sutent), sorafenib (Nexavar), axitinib (Inlyta), pazopanib (Votriento), Nivolumab (OPDIVO), pembrolizumab, ipilimumab (YERVOY), vemurafenib (ZELBORAF), everolimus (AFINITOR), temsirolimus (TORISEL), rituximab (Rituxan), bevacizumab (Avastin), geldanamycin and the like.

The anticancer agent may also be an anti-angiogenic agent. The anti-angiogenic agent may be one that inhibits vascular endothelial growth factor (VEGF) or other angiogenic factor, or a receptor thereof. Specific examples of the anti-angiogenic agent include angiostatin, endostatin, metastatin, anti VEGF antibody (e.g., Avastin), VEGFR-2 inhibitor (e.g., SU5416, SU6668), and the like.

(Detectable Substance)

In the present specification, the detectable substance refers to any substance that makes the conjugate of the present invention containing the substance detectable. Preferably, the detectable substance enables detection of the conjugate of the present invention in vivo directly or indirectly using an appropriate visualization or imaging means. Examples of the visualization or imaging means include, but are not limited to, X-ray photography, computed tomography (CT), nuclear magnetic resonance imaging (MRI), ultrasonography, scintigraphy, positron emission tomography (PET), endoscopy, laparoscopy, and the like. The detectable substance may be, for example, a radioisotope, an enhancing agent for MRI (e.g., paramagnetic ions), a radiopaque substance, a contrast agent, a fluorescent substance, or the like.

Examples of the radioactive nuclide useful for PET include $^{18}$F, $^{51}$Mn, $^{52m}$Mn, $^{52}$Fe, $^{55}$Co, $^{62}$Cu, $^{64}$Cu, $^{64}$Cu, $^{68}$Ga, $^{72}$As, $^{75}$Br, $^{76}$Br, $^{82m}$Rb, $^{83}$Sr, $^{86}$Y, $^{89}$Zr, $^{94m}$Tc, $^{110}$In, $^{120}$I, $^{124}$I and the like. Examples of the radioactive nuclide useful for detection of γ ray include $^{51}$Cr, $^{57}$Co, $^{58}$Co, $^{59}$Fe, $^{67}$Cu, $^{67}$Ga, $^{75}$Se, $^{97}$Ru, $^{99m}$Tc, $^{111}$In, $^{114m}$In, $^{123}$I, $^{125}$I, $^{131}$I, $^{169}$Yb, $^{197}$Hg, $^{201}$Tl and the like.

Preferable examples of the paramagnetic ion include chromium (III), manganese (II), iron(III), iron(II), cobalt(II), nickel(II), copper(II), neodymium (III), samarium (III), ytterbium (III), gadolinium (III), vanadium (II), terbium (III), dysprosium (III), holmium (III), erbium (III) and the like, and gadolinium is particularly preferable. In addition, metals such as lanthanum (III), gold (III), lead (II), bismuth (III) and the like are also useful for X-ray imaging and the like.

Examples of the radiopaque substance and contrast agent include iodine compounds (for example, organic iodic acids such as iodocarboxylic acid, iodoform, triiodophenol, tetraiodoethylene, etc.), barium compounds (for example, barium sulfate and the like), gallium compounds (such as gallium citrate), thallium compounds (such as thallium chloride) and the like.

Examples of the fluorescent substances include rhodamine, fluorescein, Cy dye, Alexa (registered trademark) Fluor, phycoerythrin (PE), allophycocyanin (APC), derivatives thereof and the like. Near infrared fluorescent reagents such as indocyanine are also exemplified as preferable fluorescent substances.

(Binding of Peptide of the Present Invention with Component)

The mode of binding of the peptide of the present invention with one or more components in the conjugate of the present invention is not particularly limited. The binding may be direct or indirect via a linker etc. The binding may be by covalent binding, non-covalent binding, or a combination thereof. One or more components may be directly or indirectly bonded at the N-terminal, C-terminal, or other position of the peptide of the present invention. The binding of a peptide with other component (or second peptide) is well known in the art, and the binding may be by any known means in the conjugate of the present invention.

For example, when the binding is via a linker, known crosslinkers such as NHS ester, imide ester, maleimide, carbodiimide, allyl azide, diaziline, isocyanide, psoralen and the like can be used. Depending on the crosslinker to be used, the peptide of the present invention may be modified as appropriate. For example, a cysteine can be added in advance to the C-terminal of the peptide of the present invention for binding with a maleimide linker.

For linking radioactive metal or paramagnetic ion mentioned above to the peptide of the present invention, an appropriate chelating agent (e.g., ethylenediaminetetraacetic acid (EDTA), diethylenetriaminepentaacetic acid (DTPA), 4,7,10-tetraazacyclododecane-N—N',N",N'"-tetraacetic acid (DOTA) and the like) and/or metallothionein and the like can be used. See, for example, Culali Aktolun et al. ed., "Nuclear Medicine Therapy: Principles and Clinical Applications", Springer, 2013 and the like.

3. Composition

The present invention also provides a composition containing the peptide or conjugate of the present invention and a pharmacologically acceptable carrier (hereinafter to be also referred to as the composition of the present invention. The composition may be provided in a dosage form suitable for oral or parenteral administration.

Examples of the composition for parenteral administration include injection, suppository and the like. The injection may include dosage forms such as intravenous injection, subcutaneous injection, intradermal injection, intramuscular injection, drip intravenous injection, and the like. Such injections can be prepared according to a known method. As a method for preparing an injection, for example, the peptide or conjugate of the present invention can be prepared by dissolving, suspending or emulsifying the peptide or conjugate of the present invention in a sterile aqueous solution or oily solution generally used for injection. As an aqueous solution for injection, for example, physiological saline, an isotonic solution containing glucose and other adjuvant may be used and may be used in combination with suitable solubilizing agents such as alcohols (e.g., ethanol), polyalcohols (e.g., propylene glycol, polyethylene glycol), non-ionic surfactants (e.g., polysorbate 80, HCO-50 (polyoxyethylene (50 mol) adduct of hydrogenated castor oil)), and the like. As the oily solution, for example, sesame oil, soybean oil, or the like is used, and benzyl benzoate, benzyl alcohol, or the like may be used in combination as a solubilizing agent. The prepared injection solution is preferably filled in a suitable ampoule. A suppository to be used for rectal administration can be prepared by mixing the peptide or conjugate of the present invention with a conventional base for suppository.

The composition for oral administration includes, for example, solid or liquid dosage forms, specifically tablet (including sugar-coated tablet, film-coated tablet), pill, granule, powder, capsule (including soft capsule), syrup, emulsion, suspension, and the like. Such compositions are produced by a known method and may contain carrier, diluent or excipient generally used in the field of preparations. As the carrier and excipient for tablets, for example, lactose, starch, sucrose, magnesium stearate are used.

Each of the above-mentioned compositions may contain other active ingredient as long as blending with the above-mentioned peptide or conjugate does not cause an undesirable interaction.

The above-mentioned parenteral or oral pharmaceutical compositions are conveniently formulated in a dosage unit form compatible with the dosage of the active ingredient. Examples of the dosage form for such dosage unit include tablet, pill, capsule, injection (ampoule) and suppository. The content of the peptide or conjugate is generally preferably 1 to 500 mg per dosage unit form, preferably, in particular, 1 to 100 mg for injection, and 10 to 250 mg for other dosage forms.

The composition of the present invention can target tumor, particularly angiogenic malignant tumor, and preferably can accumulate the peptide or conjugate in the tumor. Thus, the composition of the present invention containing an anticancer agent in the conjugate is useful for the treatment or prevention of the targeted malignant tumor. The composition of the present invention containing a detectable substance in the conjugate is also useful for the examination or diagnosis of malignant tumor.

The malignant tumor (cancer) may be any kind of cancer, and may also be solid cancer or liquid cancer. As the solid cancer, those that express Anxa1 on the cell surface, and therefore, solid tumors that are angiogenic, are preferably mentioned. Examples of the solid cancer include cancer of the brain/nervous system (e.g., brain tumor, spinal cord tumor etc.), head and neck cancer (e.g., laryngeal cancer, oral cancer, salivary gland cancer, paranasal sinus cancer, thyroid cancer etc.) digestive organ cancer (e.g., stomach cancer, esophageal cancer, small intestine cancer, colon cancer, rectal cancer, anal cancer, liver cancer, biliary tract cancer, pancreatic cancer etc.), urinary or reproductive organ cancer (e.g., kidney cancer, kidney cell cancer, bladder cancer, prostate cancer, renal pelvis and ureter cancer, gall bladder cancer, bile duct cancer, testis cancer, penile cancer, uterine cancer, endometrial cancer, uterine sarcoma, cervical cancer, vaginal cancer, vulvar cancer, ovarian cancer, fallopian tube cancer and the like), respiratory system cancer (e.g., lung cancer (including small cell lung cancer, non-small cell lung cancer, metastatic lung cancer), bronchial cancer and the like), breast cancer, skin cancer (e.g., malignant melanoma etc.), bone cancer (e.g., osteosarcoma etc.), muscle cancer (e.g., rhabdomyosarcoma etc.) and the like.

As the liquid cancer, leukemia, malignant lymphoma, multiple myeloma, myelodysplastic syndrome and the like can be mentioned. As leukemia, acute myeloid leukemia, acute lymphocytic leukemia, chronic myeloid leukemia, chronic lymphocytic leukemia and the like can be mentioned. The malignant lymphoma is classified into Hodgkin lymphoma and non-Hodgkin's lymphoma, and examples of non-Hodgkin's lymphoma include B cell lymphoma, adult T cell lymphoma, lymphoblastic lymphoma, diffuse large cell lymphoma, Burkitt lymphoma, follicular lymphoma, MALT lymphoma, peripheral T cell lymphoma, mantle cell lymphoma and the like.

Since the peptide or conjugate of the present invention can efficiently cross the blood-brain tumor barrier, brain tumor can be recited as a particularly preferred target. The brain tumor may be a primary brain tumor or a metastatic brain tumor. The brain tumor may also be a benign brain tumor (e.g., meningioma, pituitary adenoma, schwannoma, etc.) or malignant brain tumor, preferably malignant brain tumor. Examples of the malignant brain tumor include grade 2 brain tumor s such as astrocytoma, oligodendroglioma, grade 3 brain tumor s such as anaplastic astrocytoma, anaplastic oligodendroglioma, anaplastic oligoastrocytoma, and grade 4 brain tumor s such as glioblastoma.

The composition of the present invention may be administered to an animal, particularly a mammal, expressing annexin A1. Examples of the mammal include, but are not limited to, laboratory animals such as rodents such as mouse, rat, hamster, guinea pig, and rabbit and the like, domestic animals such as pig, cow, goat, horse, sheep, mink and the like, pets such as dog, cat and the like, primate such as human, monkey, rhesus monkey, marmoset, orangutan, chimpanzee, and the like.

The dosage of the composition of the present, invention also varies depending on the purpose of administration, administration subject, target disease, condition, administration route, and the like. For example, when used for the treatment or prevention of cancer described above, it is convenient to administer the conjugate of the present invention containing an anticancer agent once a week intravenously or orally generally at 0.1 to 10 mg per kg body weight as a single dose. Alternatively, when used for testing or diagnosing cancer described above, it is convenient to administer the conjugate of the present invention containing a detectable substance intravenously or orally at generally about 0.1 to 10 mg/kg body weight prior to the testing.

EXAMPLES

The present invention is described in more detail in the following by referring to examples and the like, but the present invention is not limited by the following examples and the like.
(Preparation of Experimental Animal)

Rat glioma C6 cells were cultured in Dulbecco's Modified Eagles Medium added with 10% fetal bovine serum, high glucose and antibiotic. Lentivirus vector PGK-Luc was prepared at the Virus Core Facility of Sanford-Burnham-Prebys Medical Discovery Institute. C6 cell and B16 cell were infected with PGK-Luc lentivirus and luciferase positive cells were produced. Using a stereotactic frame, C6-Luc cells ($4.8 \times 10^4$ cells suspended in 4 μl PBS) were injected into the brain corpus striatum of C57BL/6 mouse. Two days later, the mouse was imaged for tumors expressing luciferase. To this end, 100 μl of luciferin (30 mg/ml PBS) was injected into the peritoneal cavity, the mouse was anesthetized with isoflurane gas (20 ml/min) together with oxygen (1 ml/min) and placed under a camera provided with Xenogen IVIS 200 imager. The photon number was measured for 1-10 seconds. For the dual tumor model, C6-Luc cells were similarly injected into the brain of NOD-SCID mouse and tumor growth was monitored by Xenogen imager.

When the brain tumor became detectable, C6-Luc cells ($2 \times 10^5$ cells suspended in 100 μl PBS) were subcutaneously injected into the dorsal flank of the same mouse. The photon number in the brain tumor and subcutaneous tumor was measured using Xenogen imager. A dual tumor model of the same strain C57BL/6 mouse was also prepared using B16-Luc cells. B16-Luc cells ($5 \times 10^4$ cells) were injected into the brain of 8- to 10-week-old C57BL/6 female mouse as described above for C6-Luc cells. B16-Luc cells ($2 \times 10^5$ cells) were subcutaneously injected when B16-Luc tumor in the brain became detectable.

Examination Example 1: Administration Experiment of IF7 to Tumor-Bearing Mouse

IF7 (i.e., L form peptide having the amino acid sequence of IFLLWQR (SEQ ID NO: 10)) was intravenously administered to a tumor-bearing mouse. After reaching the blood vessels around the tumor, IF7 was taken into the vesicle from the luminal side of vascular endothelial cells, moved to the basal side and was released to the stroma where cancer cells were present.

Even in mouse vascular endothelial F2 cells, IF7 bound to Anxa1 actively transected tumor vascular endothelial cells by transcytosis. Therefore, it was suggested that IF7 has an activity to cross the vascular-brain tumor barrier in the brain tumor.

Figure 2:
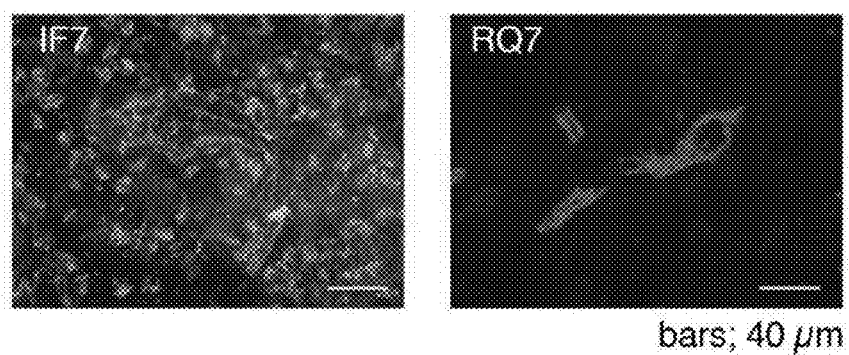
FIG. 2 shows a fluorescence microscopic image of brain tumor tissue section from mouse treated with the fluorescently labeled IF7. An enlarged view of the brain tumor tissue section shown in FIG. 1. Vascular endothelial cell was stained with CD31 specific antibody (red). IF7-A488 (green) passed through blood vessels to reach cancer cells in the stroma. RQ7 is an inverse sequence control of IF7. Bars; 40 µm.

Surprisingly, when fluorescently labeled IF7 was intravenously injected into a brain tumor model mouse transplanted with glioma cells, accumulation of fluorescence at a high concentration was observed in the brain tumor site (FIGS. 1 and 2). In addition, fluorescence crossed the blood vessel and reached cancer cells in the brain stroma.

Examination Example 2: Administration Experiment of IF7-SN38 to Dual Tumor Model Using a mouse within which both subcutaneous tumor and brain tumor are present (dual tumor model), the treatment effect of IF7-SN38 was verified. The experiment was conducted as follows.

IF7C(RR)-SN38 was injected into the tumor-bearing mouse via the tail vein when the photon number of the brain tumor became $>1.0 \times 10^6$ (this generally occurred 2 weeks later). IF7C(RR)-SN38 (14.2 mg or 6.63 mmol) was dissolved in 100 μl of dimethyl sulfoxide (DMSO), 1 μL of the solution (142 mg or 66.3 nmoles) was diluted with 50% ethanol solution (10 μl) of Cremophore EL, and 90 μl of PBS was further added. The IF7C(RR)-SN38 amount per injection was 142 mg/mouse or 7.1 mg/kg. The inverse sequence of IF7 or RQ7C(RR)-SN38 prepared similarly was used as a control. Irinotecan dissolved in PBS and PBS alone were used as a negative control.

Figure 3:
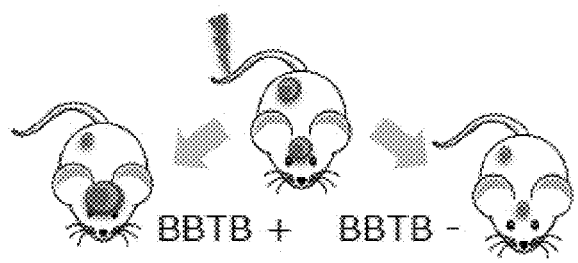
FIG. 3 explains a Dual Tumor Model Mouse. To investigate the influence on the vascular-brain tumor barrier (BBTB), luciferase (Luc)-expressing cancer cells were transplanted into the brain and under the skin of one mouse to create a tumor. When BBTB inhibits penetration of the anticancer drug administered via the tail vein into the brain tumor (BBTB+), the effects of the anticancer drug appear only in the subcutaneous tumor. On the other hand, when the anticancer drug penetrates the brain tumor (BBTB−), it is effective in both the brain and subcutaneous tumors.
Figure 4:
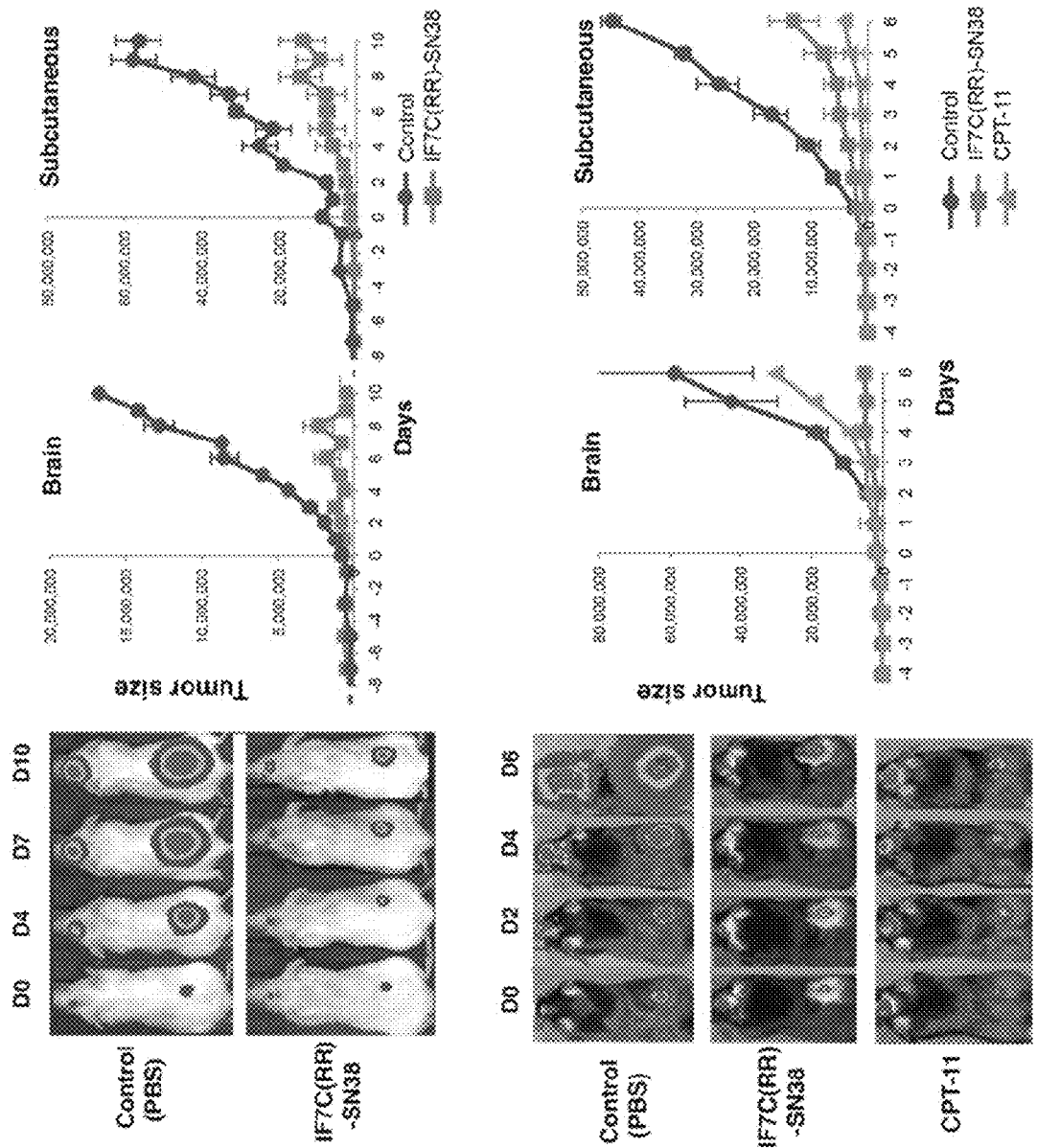
FIG. 4 shows therapeutic effects of IF7-SN38 on brain tumor. C6-Luc cells (cells forcedly expressing luciferase in rat glioma) were transplanted into the brains and under the skin of immunodeficient SCID mouse to create tumor to give a dual tumor model. IF7-SN38 was administered daily via the tail vein, luminescence due to luciferase activity in the tumor was measured and viability of C6-Luc cells was determined. IF7-SN38 not only inhibited the growth of brain tumor, but also inhibited brain tumor more strongly than the subcutaneous tumor.

As a result, both the brain tumor and the subcutaneous tumor were suppressed, and the effect thereof was higher in the brain tumor than in the subcutaneous tumor (FIGS. 3 and 4). Similar results were obtained in the B16 melanoma metastatic brain tumor model, and the results did not change even when the host mouse was changed to C57BL/6 or SCID strain. These facts indicate that DDS targeting Anxa1 not only efficiently crosses the blood-brain tumor barrier, but also provides an excellent therapeutic effect in the brain tumor irrespective of the tumor cell type and mouse strain.

Examination Example 3: Study of Pharmacokinetics of IF7

Figure 5:
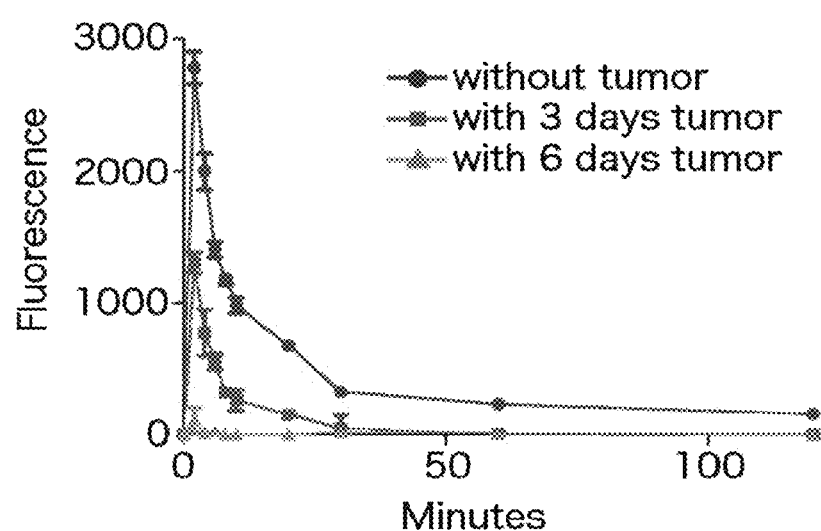
FIG. 5 shows quantitative analysis of fluorescence remaining in the blood of A488-IF7 administered intravenously to cancer bearing mice and healthy mice. A488-IF7 was administered via the tail vein to mice with subcutaneous carcinoma of melanoma B16, and peripheral blood was collected from the ocular vein over time and fluorescence was measured. The recovered fluorescence decreased depending on the size of the tumor.

As demonstrated in Examination Examples 1 and 2, IF7 has a superior malignant tumor targeting activity. In terms of clinical development, however, there are problems in two points: poor solubility and low stability. That is, IF7 peptide is protease sensitive and is susceptible to degradation. Indeed, in an experiment including intravenous administration of A488-IF7 to healthy mouse, the fluorescence signal of peripheral blood almost disappeared in about 1 hour (FIG. 5). However, with tail vein administration to tumor-bearing mouse, fluorescence recovered from the peripheral blood of A488-IF7 was markedly lower than that in healthy mice. This result suggests that A488-IF7 is mostly accumulated rapidly in the tumor while being degraded. In addition, IF7 has high hydrophobicity and causes difficulty in dosage form such as the need for addition of a surfactant after dissolution in DMSO, in an attempt to avoid precipitation when a compound bound with an anticancer drug is intravenously administered.

Example 1: Identification of dTIT7 Peptide

The present inventors considered that a more superior therapeutic agent could be created once the above-mentioned weakness associated with IF7 was overcome, and started to develop a next generation peptide consisting of a novel sequence.

Figure 6:
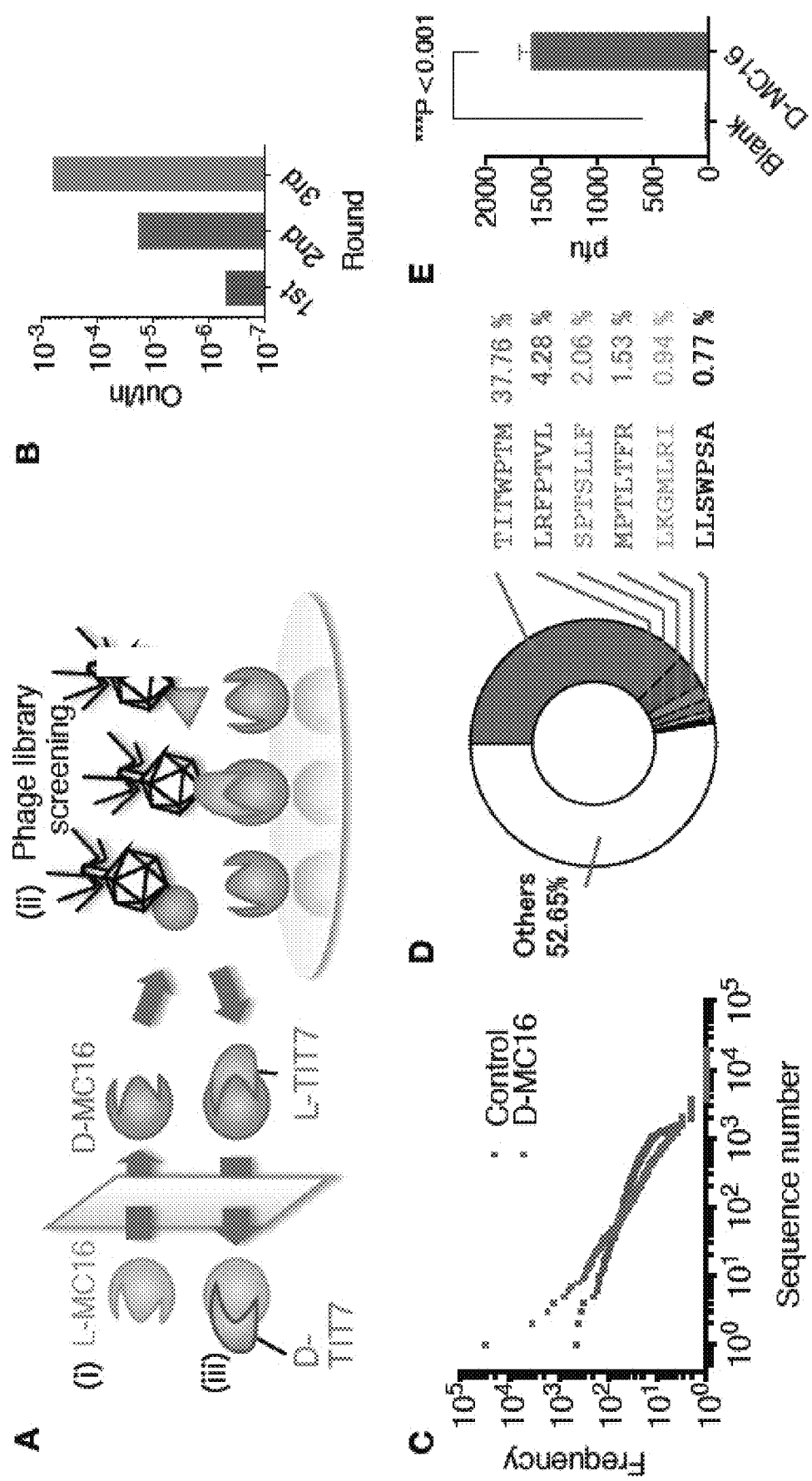
FIG. 6 explains screening for D-form peptide that binds to Anxa1. (A) D-form peptide sequence identification method by mirror image screen. IF7 binds to Anxa1 N terminal peptide ((1) L-form MC16) consisting of 16 amino acid residues. (2) D-form MC16 is synthesized and the sequence binding thereto is selected. (3) The obtained L-form peptide is synthesized with D-amino acid to form a D-form peptide that binds to Anxa1. (B) Screening results of T7 phage library targeting D-MC16. Phage enrichment was seen for each round. (C) Sequence analysis of D-MC16 specific T7 phages by next-generation sequencer. (D) Enriched peptides and proportion thereof. (E) Confirmation of binding of TIT7 phage to D-MC16 (plaque formation experiment).

The technique to be the basis of this research is a method of screening a phage library that displays on the surface about 1 billion ($20^7$ species) of random peptides consisting of 7 amino acid residues. All amino acids constituting living organisms are L-form amino acids except for some exceptions. Therefore, it is not possible to obtain the sequence of a D-form peptide that binds to the target by general phage library screening. Therefore, a mirror image screening using a T7 phage library (Funke et al., Mol. Biosystem. 2009, 783-6) was newly performed (FIG. 6).

Screening was performed based on the following findings and assumptions to obtain a phage having high binding affinity to Anxa1. It has been clarified that IF7 interacts with the N-terminal 15 residues of Anxa1 (MAMVSEFLKQAW-FIE; SEQ ID NO: 11), and that IF7 binds to L-peptide with 16 residues (L-MC16) which is Axna1 added with Cys residue for modification to the N-terminal 15 residues thereof (Sasai et al., unpublished). First, D-MC16 (all 16 bases are D-form) which is in mirror image relation with L-MC16 was synthesized and 7 amino acids (L-form TIT7 peptide) that bind to D-MC16 were identified by screening using T7 phage library. Based on the obtained sequence, TIT7 peptide (dTIT7) composed of D-form amino acids was synthesized. This dTIT7 peptide is expected to bind to Anxa1.

When analyzing the peptide sequence displayed by the phage, it was a general practice to optimize the sequence by introducing various mutations into the peptide sequence. Currently, it is possible to evaluate and identify the optimal peptide sequences at once from the sequences of not less than 10,000 candidate peptides by applying the obtained phage groups to the next generation DNA sequencer.

Analysis results revealed that the frequency of appearance of 7 amino acids starting with TIT (threonine-isoleucine-threonine) is high as a sequence binding to the N-terminal part of Anxa1, and among them, the TIT7 sequence "TITWPTM" (SEQ ID NO: 12) is prominent. While the frequency of the partial sequence of TIT7 also appeared in the top ranking position, no sequence substitute of TIT7 was found. In addition, the peptide of TIT7 was composed of a novel sequence completely different from the sequence of IF7 (IFLLWQR; SEQ ID NO: 10).

The above results showed that straight chain peptide TIT7 of seven amino acids that consists of all D-form amino acids was successfully obtained.

Furthermore, when the intermolecular interaction between dTIT7 and Anxa1 was measured by the QCM method, the dissociation constant (Kd value) was $4.57 \times 10^{-8}$ M.

As shown in FIG. 6D, peptides with sequences of LRFPTVL (SEQ ID NO: 13), SPTSLLF (SEQ ID NO: 14), MPTLTFR (SEQ ID NO: 15), LKGMLRI (SEQ ID NO: 16) and LLSWPSA (SEQ ID NO: 17) frequently appeared in addition to the TIT7 sequence (SEQ ID NO: 12), and among the vast number of $10^9$ species of random peptides, these six peptides occupied about 50% of the whole.

Figure 7:
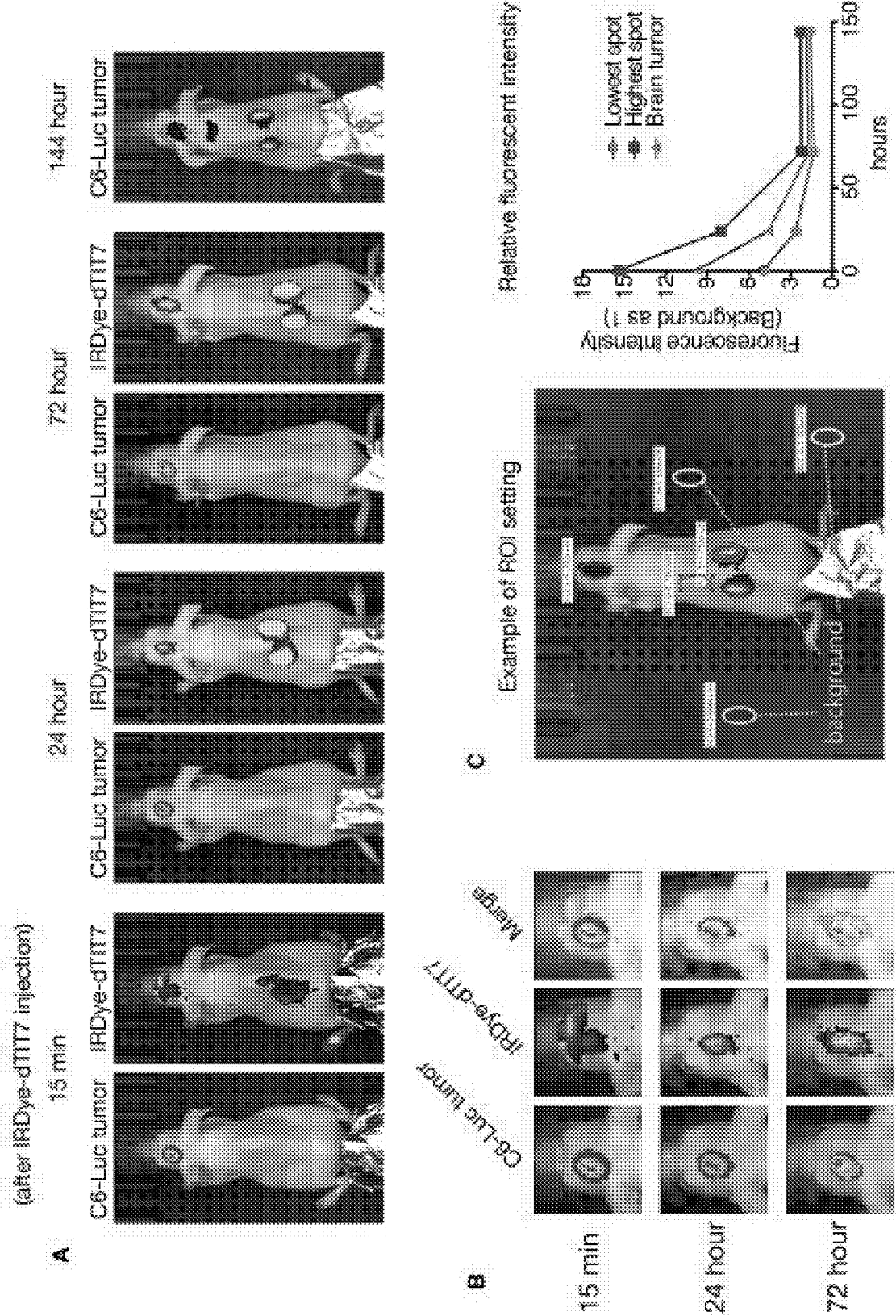
FIG. 7 shows the results of IRDye-dTIT7 administration experiment. Rat glioma cells (C6-Luc) forcedly expressing luciferase were transplanted into the brain of nude mouse to prepare a brain tumor model mouse. dTIT7 (IRDye-dTIT7, unpurified product) labeled with near-infrared fluorescent reagent (IRDye 800CW)) was injected into the tail vein, and fluorescence was observed over time by IVIS Imager. Accumulation of fluorescence signals was observed in the brain tumor site and kidney after 24 hours. (A) Overall image over time (B) Enlarged photograph (C) Signal quantification by a software of IVIS imager.

Example 2: Brain Tumor Targeting Ability of dTIT7 Peptide dTIT7 (IRDye-dTIT7) labeled with near infrared fluorescent reagent IRDye 800CW was prepared. A brain tumor nude mouse model in which rat glioma was transplanted into the brain of the mouse was prepared and IRDye-dTIT7 was injected via the tail vein of the mouse. As a result, it was observed by in vivo imaging that IRDye-dTIT7 accumulates at the tumor site of a brain tumor model mouse (FIG. 7).

Example 3: Antitumor Effect of dTIT7-Bound Anti-Cancer Agent on Brain Tumor Model Next, the effect of dTIT7-anticancer agent conjugate on brain tumor model mouse was examined.

Figure 8:
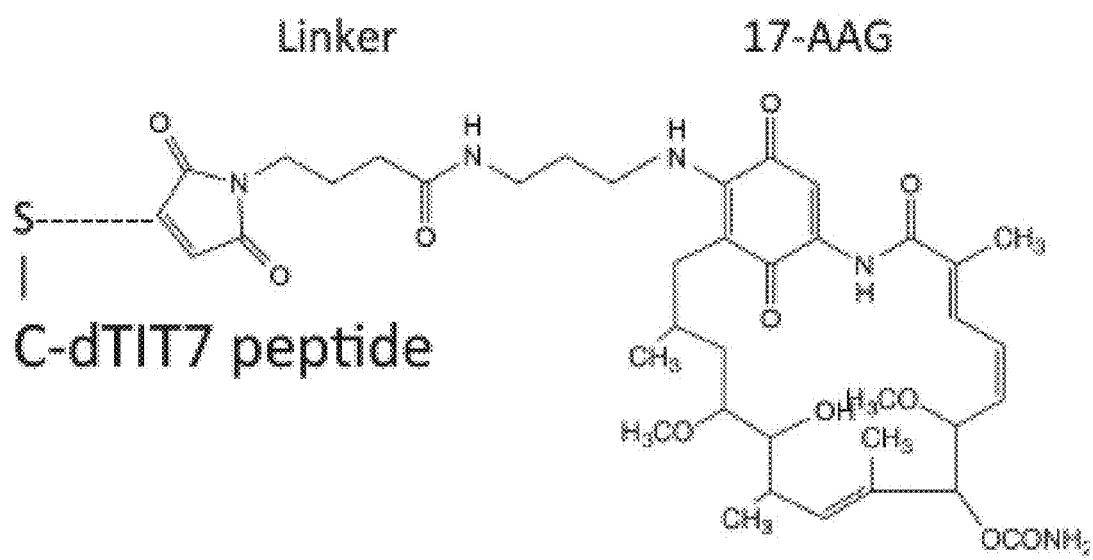
FIG. 8 shows the structure of GA-dTIT7 condensate. An amino group is introduced into geldanamycin to bind a maleimide linker. Cysteine is added in advance to the C-terminal of dTIT7 to perform the synthesis. It is reacted with maleimide via the sulfhydryl group of the cysteine residue to give GA-dTIT7 condensate.

GA-dTIT7 in which an anticancer drug geldanamycin was bound to dTIT7 peptide (FIG. 8) is resistant to both protease and esterase and is considered to be more stable in vivo. GA-dTIT7 at a 1/10-fold (in terms of molar number) of the recommended dose was intravenously administered to a tumor-bearing mouse (melanoma B16 cells, subcutaneously administered) every 1 or 2 days. As a result, tumor growth was remarkably suppressed, and a large amount of necrosis was observed at the tumor site of mouse administered with GA-dTIT7 by histopathological observation. This effect strongly suggests the possibility that dTIT7 is superior to IF7 which required consecutive administration (Hatakeyama et al., Proc. Natl. Acad. Sci USA, 108: 19587-92, 2011).

Figure 9:
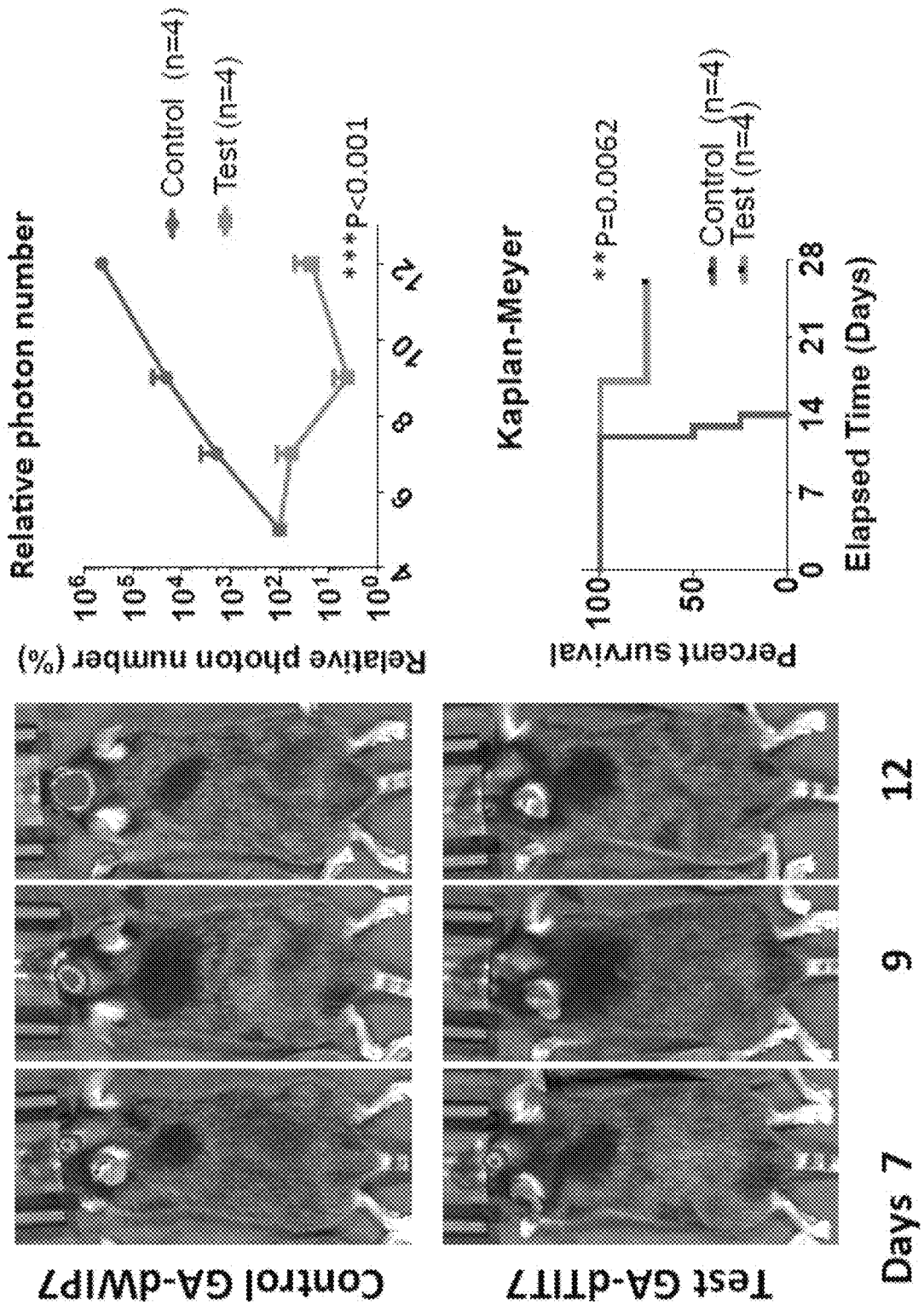
FIG. 9 shows the results of experiment including oral administration of a drug of dTIT7 bound with an anticancer agent gerdanamycin (GA) (GA-dTIT7) to a brain tumor model mouse every other day. Survival of brain tumor was quantified by luminescence by luciferase. GA-dWIP7 containing WIPTTMT (peptide in which the order of D-amino acid sequence constituting dTIT7 was changed) bound with geldanamycin was administered as a control to a mouse. A graph (upper right) quantifying the viable cell signal (left) of the malignant tumor and the survival curve (lower right) are shown.
Figure 10:
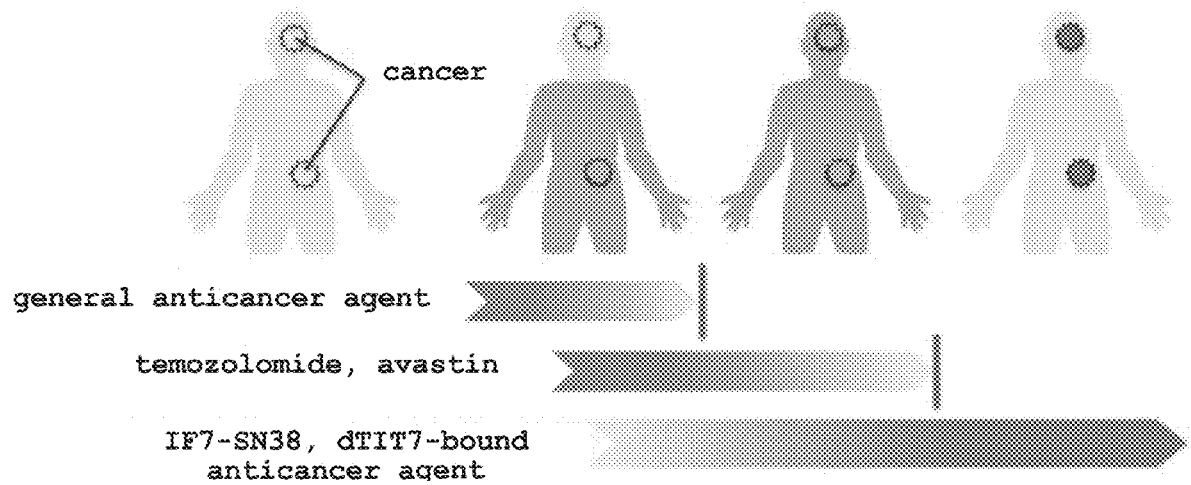
FIG. 10 conceptually explains the targeted treatment of malignant brain tumor with an IF7, dTIT7-bound anticancer agent. For convenience, the blood-brain barrier was considered to be present above the neck. General anticancer drugs do not have a tumor targeting ability. Temozolomide penetrates into brain tumor to some extent but is not concentrated. Avastin acts on new blood vessels but does not act directly on tumor cell. In contrast, Anxa1-bound peptide crosses the blood-brain tumor barrier and accumulates only in tumor at a high concentration.

More surprisingly, when GA-dTIT7 was orally administered to a brain tumor model transplanted with B16 cells into the brain, tumor regression was observed, the tumor continued to decrease even after administration of the drug was stopped, and finally, complete cure was observed in 2 out of 4 mice (FIG. 9). Similar therapeutic effects were also observed in a brain tumor model using C6 cells. This suggests that GA-dTIT7 may lead to the complete cure of brain tumor as an anticancer agent that can be administered orally.

Example 4: Intermolecular Interaction Between dLRF7, dSPT7, dMPT7 and dLLS7 Peptides and Anxa1

As for the peptides of the sequences of LRFPTVL (SEQ ID NO: 13), SPTSLLF (SEQ ID NO: 14), MPTLTFR (SEQ ID NO: 15) and LLSWPSA (SEQ ID NO: 17) with high emergence frequency besides the TIT7 sequence (SEQ ID NO: 12) described in Example 1, similar to the dTIT7 peptide, peptides (dLRF7, dSPT7, dMPT7 and dLLS7 peptides) composed of D-form amino acids were synthesized and the intermolecular interaction with Anxa1 was measured for each of them by the following method.

The sensor chip was washed twice with piranha solution for 5 min and then immersed overnight in a solution of 0.9 mM hydroxy-EG3-undecanethiol (Dojindo) and 0.1 mM amino-EG6-undecanethiol (Dojindo). After washing with water, the chip was treated with 1 mM GMBS (Dojindo) and incubated at room temperature for 1 hr. After washing away the remaining GMBS, 1 mM peptide solution was added onto the chip and the chip was incubated for 30 min. The peptide-bound sensor chip was placed in a QCM apparatus (Single-Q, ASONE), and 0.5 ml of PBS was added to the well. Various doses of Anxa1 were injected into the reaction chamber and the binding affinity (kd value) for each peptide was determined.

Figure 11:
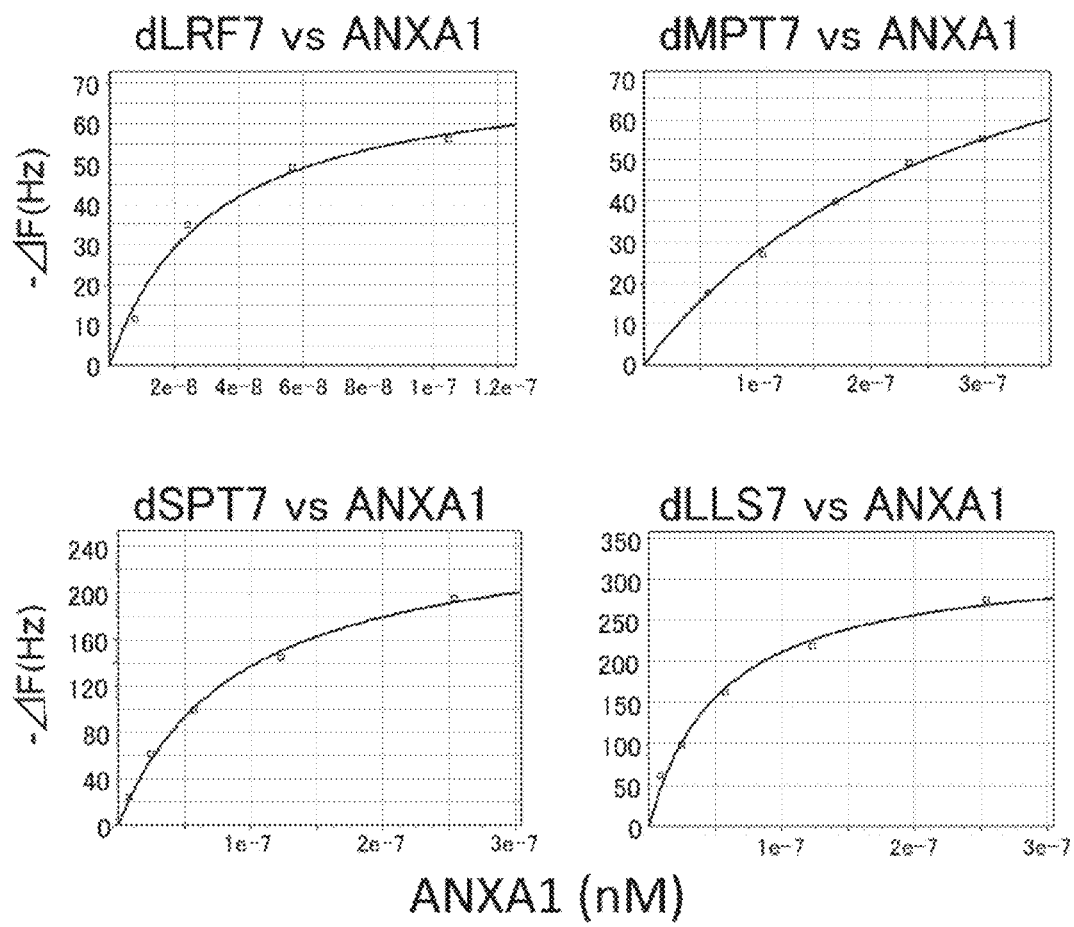
FIG. 11 shows the results of intermolecular interactions of Anxa1 with dLRF7, dSPT7, dMPT7 and dLLS7 peptides. All peptides tested showed positive binding to Anxa1.

As a result, all peptides tested showed positive binding to Anxa1 (Table 1 and FIG. 11).

TABLE 1

| name of synthetic peptide | kd value (M) |
| --- | --- |
| dLRF7 | $3.119 \times 10^{-8}$ |
| dSPT7 | $9.029 \times 10^{-8}$ |
| dMPT7 | $2.982 \times 10^{-7}$ |
| dLLS7 | $5.418 \times 10^{-8}$ |

Example 5: Brain Tumor Targeting Ability of dLRF7, dSPT7, dMPT7 and dLLS7 Peptides DLRF7, dSPT7, dMPT7 and dLLS7 peptides which were extended by adding terminal cysteine were chemically synthesized. Then, each peptide was bound to near infrared fluorescent dye IRDye 800CW maleimide (Li-Cor) via a cysteine residue. The resulting peptide conjugate was purified by HPLC and then lyophilized. Each peptide-IRDye conjugate was dissolved in DMSO and 6% glucose and intravenously injected into brain tumor model nude mouse at 100 µl/mouse. After 24 hr, the fluorescence image was measured by IVIS spectrum (Perkin Elmer).

Figure 12:
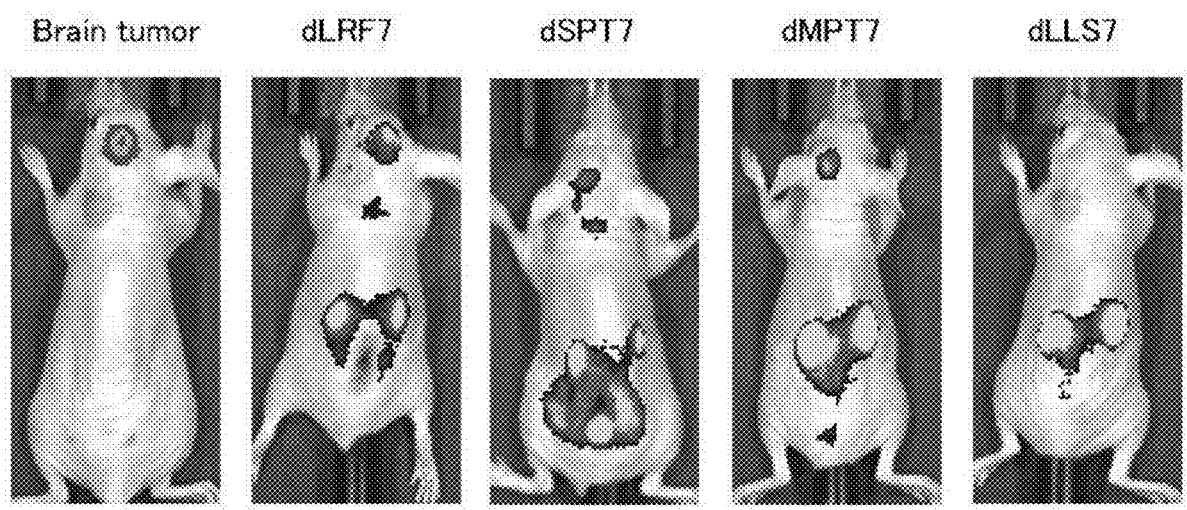
FIG. 12 shows the experiment results of administration of IRDye-dLRF7, IRDye-dSPT7, IRDye-dMPT7 and IRDye-dLLS7 to brain tumor model nude mice. All mice, except those injected with dLLS7, showed strong signals at the brain tumor site, and three peptides of dLRF7, dMPT7 and dSPT7, other than dLLS7, showed a brain tumor targeting ability via the vasculature route.

As a result, all mice except those injected with dLLS7 showed a strong signal of IRDye at the brain tumor site, and three peptides dLRF7, dMPT7 and dSPT7 other than dLLS7 showed a brain tumor targeting ability via the vasculature pathway (FIG. 12).

This application is based on a patent application No. 2016-159743 filed in Japan (filing date: Aug. 16, 2016), the contents of which are incorporated in full herein.

The invention claimed is:

1. A peptide comprising the amino acid sequence of T[D] I[D] T[D] W[D] P[D] T[D] M[D], wherein each amino acid symbol immediately followed by symbol [D] is a D form of the amino acid.

2. The peptide according to claim 1, consisting of the amino acid sequence of T[D] I[D] T[D] W[D] P[D] T[D] M[D], wherein each amino acid symbol immediately followed by symbol [D] is a D form of the amino acid.

3. A conjugate comprising the peptide according to claim 1 linked to one other component.

4. The conjugate according to claim 3, wherein the one other component is an anticancer agent.

5. The conjugate according to claim 4, wherein the anticancer agent is selected from the group consisting of an antimetabolite, an alkylating agent, an anticancer antibiotic, a microtubule inhibitor, a platinum preparation, a topoisomerase inhibitor, a molecular targeting agent, and an anti-angiogenic agent.

6. The conjugate according to claim 3, wherein the one other component is a detectable substance.

7. The conjugate according to claim 6, wherein the detectable substance enables detection of the conjugate in vivo by a means selected from the group consisting of X-ray photography, computed tomography (CT), nuclear magnetic resonance imaging (MM), ultrasonography, scintigraphy, positron emission tomography (PET), endoscopy and laparoscopy.

8. The conjugate according to claim 6, wherein the detectable substance is a radioisotope, an MM enhancer, a radiopaque substance, a contrast agent or a fluorescent substance.

9. The conjugate according to claim 7, wherein the detectable substance is a radioisotope, an MM enhancer, a radiopaque substance, a contrast agent or a fluorescent substance.

10. A composition comprising the peptide according to claim 1 and a pharmacologically acceptable carrier.

11. A method of treating a subject having a solid tumor that expresses Anxa1 on the cell surface, comprising a step of administering to the subject a composition comprising the conjugate according to claim 4 and a pharmacologically acceptable carrier.

12. The method of claim 11, wherein the solid tumor that expresses Anxa1 on the cell surface is a brain tumor.

13. A method of detecting a solid tumor that expresses Anxa1 on the cell surface, comprising a step of administering to a subject a composition comprising the conjugate according to claim 6 and a pharmacologically acceptable carrier.

14. The method of claim 13, wherein the solid tumor that expresses Anxa1 on the cell surface is a brain tumor.

15. A method of treating a subject having a liquid cancer that expresses Anxa1 on the cell surface, comprising a step of administering to the subject a composition comprising the conjugate according to claim 4 and a pharmacologically acceptable carrier.

* * * * *